United States Patent [19]
Saksena et al.

[11] Patent Number: 5,698,557
[45] Date of Patent: Dec. 16, 1997

[54] HYDROXY-SUBSTITUTED ANTIFUNGALS

[75] Inventors: Anil K. Saksena, Upper Montclair; Viyyoor M. Girijavallabhan, Parsippany; Raymond G. Lovey, West Caldwell; Russell E. Pike, Stanhope, all of N.J.

[73] Assignee: Schering Corporation, Kenilworth, N.J.

[21] Appl. No.: 664,758

[22] Filed: Jun. 17, 1996

Related U.S. Application Data

[60] Provisional application No. 60/000,309, Jun. 19, 1995.
[51] Int. Cl.$^6$ .................. A61K 31/495; C07D 403/00
[52] U.S. Cl. ........................................ 514/252; 544/366
[58] Field of Search ........................... 544/366; 514/252

[56] References Cited

U.S. PATENT DOCUMENTS

| | | | |
|---|---|---|---|
| 4,791,111 | 12/1988 | Heeres et al. | 514/252 |
| 5,023,258 | 6/1991 | Gymer et al. | 514/255 |
| 5,039,676 | 8/1991 | Saksena et al. | 514/254 |

FOREIGN PATENT DOCUMENTS

| | | |
|---|---|---|
| 0 539 938 A1 | 5/1993 | European Pat. Off. . |
| WO 89/04829 | 6/1989 | WIPO . |
| WO 95/17407 | 6/1995 | WIPO . |
| WO 95/19983 | 7/1995 | WIPO . |

Primary Examiner—Matthew V. Grumbling
Assistant Examiner—Brenda Coleman
Attorney, Agent, or Firm—Thomas D. Hoffman

[57] ABSTRACT

A compound represented by the formula I

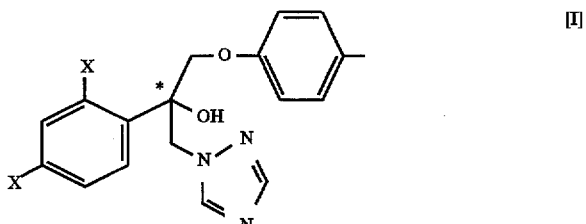

wherein X is independently both F or both Cl or one X is independently F and the other is independently Cl; $R_1$ is a straight or branched chain ($C_3$ to $C_8$) alkyl group substituted by one or two hydroxy moieties, an ether or ester thereof (e.g., a polyether ester, heterocyclic ester amino acid ester or phosphate ester) thereof and the carbon with the asterisk (*) has the R or S absolute configuration or a pharmaceutically acceptable salt thereof and pharmaceutical compositions thereof useful for treating and/or preventing fungal infections are disclosed.

19 Claims, No Drawings

HYDROXY-SUBSTITUTED ANTIFUNGALS

This application claims the benefit of U.S. Provisional Application Ser. No. 60/000,309, filed Jun. 19, 1995.

BACKGROUND OF THE INVENTION

This invention relates to hydroxy-substituted antifungals, 2-(mono- or dihydroxy substituted $C_3$–$C_8$ alkyl)-4-(4-[4-(4-[2-(2,4-dihalophenyl)-2-hydroxy-3-(1H-1,2,4-triazol-1-yl)prop-1-oxy]phenyl)piperazin-1-yl]phenyl]-1,2,4-triazolin-3-one substituted antifungals, esters, ethers and salts thereof, pharmaceutical compositions containing them, and methods of treating and/or preventing antifungal infections in hosts, including warm-blooded animals, especially humans with such hydroxy-substituted antifungals.

International Publication Number WO 89/04829, published 1 Jun. 1990 and U.S. Pat. No. 5,039,676 (A. K. Saksena et al.) discloses (±) cis and (±) (trans antifungal compounds represented by the formula

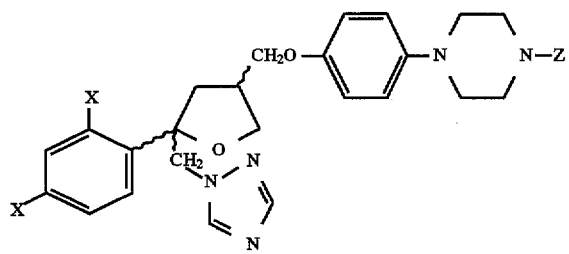

wherein X=F, Cl; Z=loweralkyl, (C2–C8) alkanoyl or phenyl substituted by 2-loweralkyl-3-oxo-1,2,4-triazol-4-yl, e.g., (±)-cis and (±)-trans-1-[4-[[2-(2,4-difluorophenyl)-2-[(1H-1,2,4-triazol-1-yl)methyl]tetrahydro-4-furanyl]methoxy]phenyl]-4-(1-methylethyl)piperazine. However, WO 89/04829 does not disclose the compounds of this invention.

Commonly-owned European Patent Publication No. 05399381, published 5 May 1993 discloses, for example, [(5R)-cis-4-[4-[4-[[5-(2,4-dihalophenyl)-5-(1H-1,2,4-triazol-1-ylmethyl) tetrahydrofuran-3-7yl]methoxy]phenyl]-1-piperazinyl]pheynyl)-2,4-dihydro-2-($C_1$–$C_{10}$)alkyl)]-3H-1,2,4-triazol-3-one antifungals but does not disclose the compounds of this invention.

Janssen U.S. Pat. No. 4,791,111 discloses, for example, (±)cis-4-[4-[4-[[2-2,4-dichlorophenyl)-2-(1H-1,2,4-triazol-1-ylmethyl)-1,3-dioxolan-4-yl]methoxy]phenyl]-1-piperazinyl]-2,4dihydro-2-(2-hydroxy-1-methylpropyl)-3H-1,2,4-triazol-3-one useful as an antimicrobial agent and having increased solubility, but does not disclose the compounds of this invention.

Pfizer U.S. Pat. No. 5,023,258 discloses certain triazole antifungals but does not disclose the compounds of this invention.

There is a need for broad-spectrum antifungal agents having increased solubility and having favorable activity profile for treating systemic fungal infections, especially Aspergillus, Candida, Cyrptococcus and opportunistic infections.

SUMMARY OF THE INVENTION

The present invention provides compounds represented by formula I

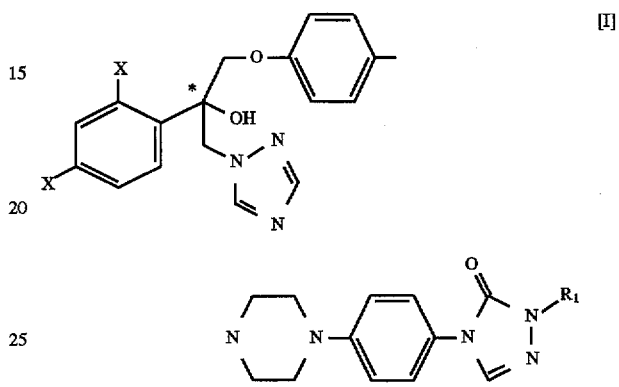

wherein

X is independently both F or both Cl or one X is independently F and the other is independently Cl;

$R_1$ is a straight or branched chain ($C_3$ to $C_8$) alkyl group substituted by one or two hydroxy moieties or stereoisomers thereof or by one or two groups convertible in vivo into hydroxy moieties or an ester or ether thereof, and wherein the carbon with the asterisk (*) has the R or S absolute configuration or a pharmaceutically acceptable salt thereof.

In a preferred aspect of the present invention, there is provided compounds represented by formula II

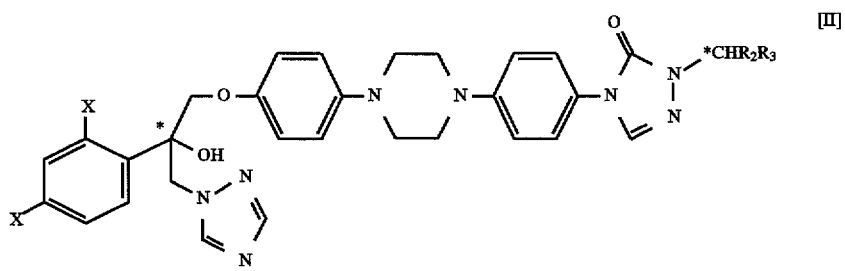

wherein

X is independently both F or both Cl or one X is independently F and the other is independently Cl; wherein $R_2$ is H or ($C_1$–$C_3$) alkyl and $R_3$ is ($C_1$–$C_3$) alkyl substituted by one hydroxy moiety or by a group convertible in vivo into a hydroxy moiety and the carbons with the asterisks (*) have the R or S absolute configuration; an ester or ether thereof or a pharmaceutically acceptable salt thereof.

In another preferred aspect, the present invention provides a compound represented by formula III

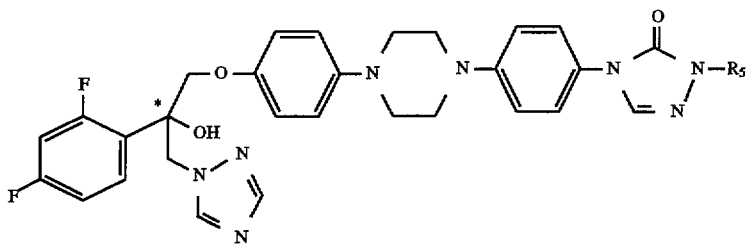

III wherein
R₅ is

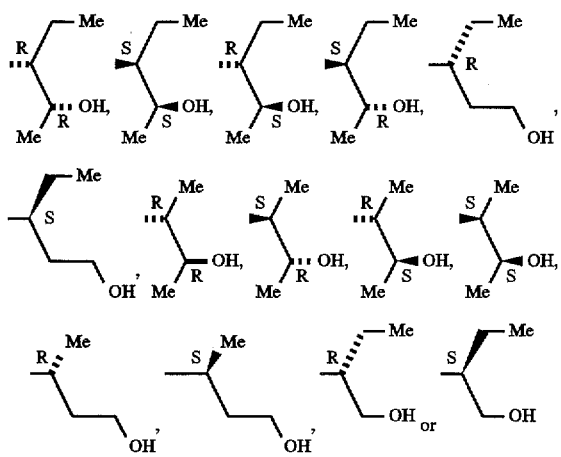

an ester thereof and the carbon with the asterisk (*) has the R or S absolute configuration or a pharmaceutically acceptable salt thereof.

Preferably the ester is a group convertible in vivo into OH e.g. a polyether ester, phosphate ester or an amino acid ester.

In another aspect of the present invention there is provided a compound represent by the formula IV

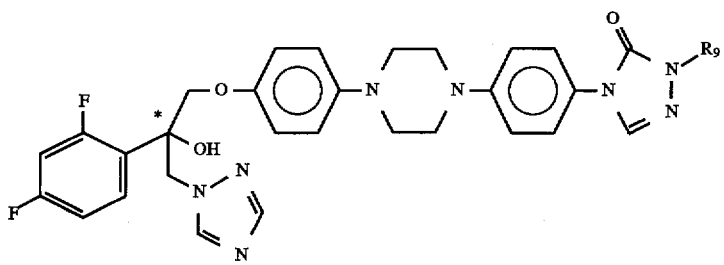

IV wherein $R_9 = \overset{*}{C}H(C_2H_5)CH(R_6)CH_3$ or $\overset{*}{C}H(CH_3)CH(R_6)CH_3$ wherein $R_6$ is OH, or a group convertible in vivo into OH and wherein the carbons with the asterisks (*) have the R or S absolute configuration or a pharmaceutically acceptable salt thereof.

DETAILED DESCRIPTION OF THE INVENTION AND OF THE PREFERRED EMBODIMENTS

The term "($C_3$–$C_8$) alkyl group substituted by one or two hydroxy moieties", as used herein means straight and branched chain alkyl groups of three to eight carbons including but not limited to methyl, ethyl, n- and iso- propyl, n-, sec, iso- and tert-butyl, n-, sec-, iso-, tert and neo-pentyl n-, sec-, iso-, tert- and neo-hexyl, n-, sec-, iso-, tert- and neo-heptyl, n, sec- iso, tert-and neo- octyl, substituted by one or two hydroxy moieties and includes R and S stereoisomers of such ($C_3$–$C_8$) alkyl groups.

The term "($C_1$–$C_3$) alkyl substituted by one hydroxy moiety" means —$CH_2OH$, —$\overset{*}{C}H(OH)CH_3$, —$CH_2CH_2OH$, —$\overset{*}{C}H(OH)C_2H_5$, —$\overset{*}{C}H_2CH(OH)CH_3$, and —$(CH_2)_3$—OH wherein the carbons with the asterisk(*) have the R or S absolute configuration.

The term "hydroxy-substituted $C_4$ or $C_5$ alkyl group" means —$\overset{*}{C}H(C_2H_5)\overset{*}{C}H(OH)CH_3$, —$\overset{*}{C}H(CH_2H_5)CH_2CH_2OH$, —$(CH_2)_2$—$\overset{*}{C}H(OH)C_2H_5$, —$\overset{*}{C}H(CH_3)\overset{*}{C}H(OH)CH_3$, —$\overset{*}{C}H(CH_3)\overset{*}{C}H(OH)CH_3$ or —$\overset{*}{C}H(C_2H_5)CH_2OH$ wherein each carbon with the asterisk (*) has the R or S absolute configuration.

The term "group convertible in vivo into OH" means a group transformable in vivo by e.g. hydrolysis and/or by an enzyme, e.g. an esterase into a hydroxyl group. Such groups include polyether esters, phosphate esters, sulfate esters, heterocyclic esters, alkanoate esters, alkenoate esters, amino acid esters and acid esters. Preferred groups convertible in vivo into a hydroxyl group are the polyether esters, phosphate esters and amino acid esters.

The term "ethers" means (a) straight and branched chain alkyloxy groups of one to twenty carbons, preferably of one to eight carbons, more preferably one to six carbons or (b) aryl($C_1$–$C_6$) alkyloxy groups of the formula —O—(CHR$_7$)$_n$—Ar wherein R$_7$ is ($C_1$–$C_6$) straight and branched chain alkyl and n=0 to 6 preferably 1 to 3 and Ar is phenyl, phenyl substituted by halo, especially chloro and fluoro, or by nitro, cyano and trihalomethyl especially trifluoromethyl. Most preferred ether groups include methoxy and benzyloxy. Such ethers are conveniently made by the well-known Williamson Ether Synthesis.

The term "esters" means (a) polyether esters (b) phosphate esters (c) heterocyclic esters (d) alkanoate and alkenoate esters (e) amino-acid esters (f) acid esters and (g) sulfate esters.

The term "polyether esters" as used herein means those polyether esters represented by the formula

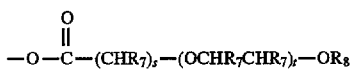

wherein $R_7$ is as defined herein and s is an integer from 1 to 6, preferably s=1 to 3 and more preferably s=1; t is an integer from 1 to 200; preferably t is 120 to 200, more preferably t is 1 to 6, and most preferably it is 1 to 3. $R^8$ is $R_7$ or $-(CHR_7)_s-CO_2R_7$; preferably $R_8$ is $CH_3$ or $C_2H_5$ or $-CH_2CO_2H$ or $-CH_2CO_2CH_3$. Typically suitable polyether esters include $-COCH_2O(CH_2CH_2O)_1CH_3$; $-COCH_2O(CH_2CH_2O))_2CH_3$, $-COCH_2O(CH_2CH_2O)_3CH_3$, $-COCH_2O(PEG_{3000})$, and $-COCH_2O(PEG_{5000})$.

The term "phosphate esters" as used herein means those phosphate acids esters represented by the formula

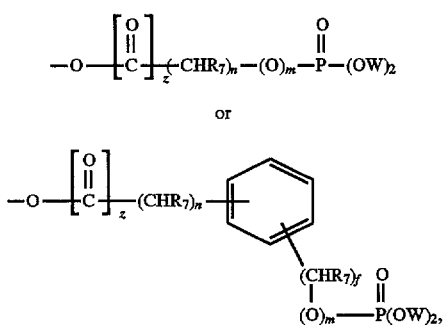

wherein z is 0 or 1; $R_7$ is as defined herein above and preferably is H; n and f are independently an integer from 0 to 6, m is 0 or 1 and W is H, $CH_2Ar$ or

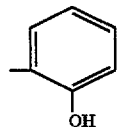

and wherein

Ar is as defined herein above. Typically suitable phosphate acids and esters include

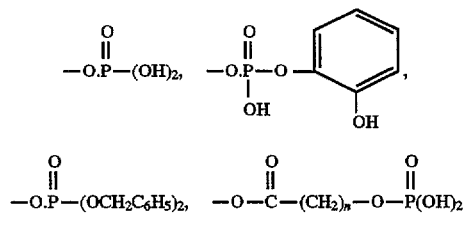

wherein m=n=1 to 4; or

and pharmaceutically acceptable salts thereof.

The term "heterocyclic ester" as used herein means heterocyclic esters represented by the formula

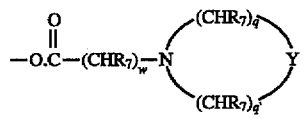

wherein $R_7$ is as defined herein above, w is an integer of from 1 to 5 preferably W is 1 to 3; q and q' are independently 1 to 4, and q+q' are preferably equal to 2, 3, 4, or 5, and Y is $CHR_7$, $-O-$, NH, $NR_7$, S, SO or $SO_2$ Typically suitable heterocyclic esters include

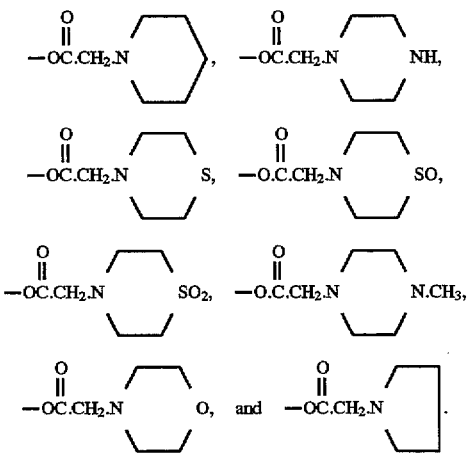

The term "alkanoate and alkenoate esters" as used herein means straight or branched chain alkanoate or alkenoate groups optionally substituted by a hydroxy or ether moiety or mixtures of such alkanoates or alkenoates.

Preferred alkanoate esters include acetate to decanoate, especially acetate to butanoate. Preferred hydroxy substituted alkanoate ester include $C_1$ to $C_8$ alkanoate substituted one hydroxy moiety or one $C_1-C_6$ alkoxy group, especially

Preferred alkenoate esters are the $C_{10}-C_{20}$ alkenoates and include $C_{14}$ to $C_{18}$ alkenoates, such as cis-7-hexadecenoate.

The term "amino acid ester" as used herein includes α-aminoalkanoyloxy, natural i.e., (L)-α-amino acid ester groups, e.g. the ester of glycine, i.e. $OCOCH_2NH_2$, peptides esters thereof, unnatural α-amino acid ester groups such as $O-CO-CH(NH_2)(CH_2)_3$ $CO_2H$, $OCOCH(NH_2)(CH)_2NH_2$, $OCOCH(NH_2)(CH)_3NH_2$ and

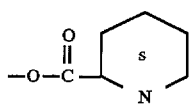

α-amino alkanoates represented by the formula —OCOCH$(NR_{20}R_{21})R_{22}$ wherein $R_{20}$ and $R_{21}$ are independently hydrogen or ($C_1$–$C_8$) straight or branched chain alkyl groups or $R_{20}$ and $R_{21}$ together with N form a 4, 5 or 6 membered ring optionally substituted with $NR_{21}$,—O— or —S— and $R_{22}$ is H, $CH_3$, $CH_2OH$, $CH(OH)CH_3$, $CH_2SH$,

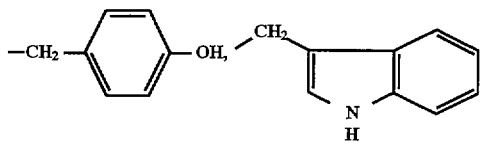

$CH_2 CONH_2$, —$(CH_2)_2CONH_2$, $CH(CH_3)_2$, $CH(CH_3)_2$, $CH(CH_3)C_2H_5$, $(CH_2)_2SCH_3$, $CH_2CO_2H$, $(CH_2)_2CO_2H$, $(CH_2)_4NH_2$—$CH_2C_6H_5$,

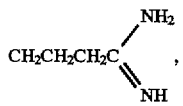

and pharmaceutically acceptable acid addition salts thereof, or ($C_1$–$C_8$) straight and branched chain alkyl groups optionally substituted by hydroxyl or $NR_{20}R_{21}$. Preferred amino acid acids are the natural α amino acid groups, dipeptides and α-amino alkanoates wherein $R_{20}$ and $R_{21}$ are each $CH_3$. The most preferred amino acid esters are those derived from alanine, phenylanine, glycine, leucine, isoleucine and valine.

The term "acid ester" as used herein means those carboxylic acid esters represented by the formula

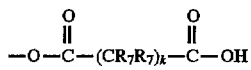

wherein $R_7$ is as defined herein above and k is an integer of from 1 to 8. Typically suitable acid esters include oxalic, malonic, succinic, glutaric and adipic acids as well as branched chain diacids such as

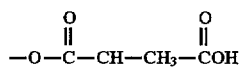

The compounds of the present invention as well as the esters thereof exhibit broad spectrum antifungal activity in various in vitro assays against Candida, other yeasts, dematophytes, Aspergillus and opportunistic fungi. The in vitro antifungal activity tests were performed via conventional broth dilution methods in Sabouraud dextrose broth ("SDB") medium and Eagles Minimum Essential Medium ("EMEM") against a large number of fungi. Minimum Inhibitory Concentrations ("MICs") were measured after 24, 48 and 72 hour tests. In many cases, Minimum Fungicidial Concentrations ("MFCS") were measured after 48 and 72 hours.

The term "opportunistic fungi" include Crytococcus, Histoplasma, Blastomyces, Coccidioides, Fusarium, Mucor, Paracoccidioides, Fonsecaea, Wangiella, Sporothrix, Pneumocystis, Trichosporon as shown by in vivo activity in an appropriate animal species e.g. mouse, rat or rabbit. The compounds of the inventions are expected to exhibit activity against many genera and species of protoza, bacteria, gram negatives, gram positives, anaerobes, including Legionella Borrelia, Mycoplasma, Treponema, Gardneralla, Trichomononas and Trypanosoma.

The preferred esters of the compounds of the present invention of formula IV are soluble and/or suspendible in an aqueous medium suitable for IV or oral administration and should exhibit superior in vivo antifungal activity against a broad range of fungi after oral and parenteral e.g. IV administration in mice, rats, dogs and monkeys.

The preferred antifungal compounds of this invention represented by formula Ia have the R absolute stereochemical configuration at the carbon bearing the hydroxy, the di-halophenyl, 1H,1,2,4-triazol-1-ylmethyl and the $CH_2O$moieties. See the formula Ia hereinbelow.

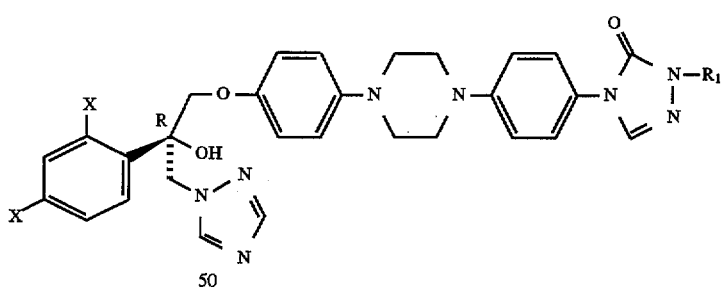

wherein $R_1$ is a straight or branched chain ($C_3$–$C_8$) alkyl group substituted by one or two hydroxy groups, which preferably exists as a single stereoisomer, but mixtures of stereoisomers are also contemplated as within the scope of this invention. Each X may be F or Cl but each X is preferably F.

GENERAL SYNTHETIC PREPARATIONS

The compounds of this invention may be prepared by use of the sequence of steps illustrated in the following Schemes I–IX. In Scheme I, compound 3 is readily prepared from commercially available compound 1 according to Examples 1a, 1b and 1c. Compound 4 is prepared by reaction of L(+)-diethyl tartarate ("L-DET") and molecular sieves in the presence of titanium tetra-isopropoxide (i-PrO)$_4$Ti in an aprotic solvent, such as methylene chloride, at a temperature 0° to −35° C. See for Example, T. Katsuki, K. B. Sharpless, *J. Am. Chem. Soc.*, 102, 5974 (1980); and 103, 464 (1981). An oxidizing agent, e.g. tert-butylhydroperoxide ("TBHP") is added to this reaction mixture (step d of Scheme I). Compound 3 is added and the compound of formula 4 (when L(+)-diethyl tartarate is used) is produced. Reaction of compound 4 with 1H-1,2,4-triazole in the presence of strong base, e.g., NaH in an aprotic solvent, such as DMF, at 0°–80° C. provides the diol compound of formula 5. The primary hydroxy group in compound 5 is converted into a leaving group, e.g., mesylate or tosylate (compound 6) by reaction of 5 with, for example, mesyl chloride ("MsCl"), in an aprotic solvent, e.g., methylene chloride in the presence of base, e.g., triethylamine ("Et$_3$N"). Compound 6 is treated with strong base, e.g., sodium hydride (NaH) in an aprotic solvent, e.g., DMF at room temperature to give oxirane compound 7. See also U.S. Pat. No. 5,023,256 Preparation 1 and EP-0228/125.

Scheme II provides a reaction sequence to obtain compounds of the present invention. Compound 9 (which may be compound 7 of Scheme I or the compound of Example 8) is reacted with the commercially available compound 10 in the presence of 2 equivalents of base, e.g. cesium carbonate in DMF and so-formed is mixture stirred overnight at 80°–90° C. to give compound 11. Catalytic reduction of 11 in the presence of a platinum or palladium catalyst yields the amine 12. Treatment of 12 with phenylchloroformate in the presence of a base, e.g. triethylamine under argon gives the urethane intermediate 13. Reaction of 13 with hydrazide 14 (see Example 25c for preparation) in the presence of DBU in toluene at 80° yields the semicarbazide 15 which is cyclized in the presence of formamidine acetate to furnish the triazolone 19. Removal of the protecting group of 19 according to Example 25e provides the compounds of structure 20F including compounds of formula I wherein R$_1$ is defined as hereinabove.

Scheme IIA provides an additional reaction sequence to obtain the compounds of the present invention. Compound 127 is prepared in accordance with preparation 5 of U.S. Pat. No. 5,023,258. Reaction of compound 127 with aqueous HBr or BBr$_3$ gives phenolic compound 128. Reaction of compound 128 with one equivalent of NaH and subsequent treatment with, for example, 2-(trimethyl)-silylethoxymethyl chloride ("SEM-Cl")and DMF at ambient temperatures produces SEM-protected compound 129. Deprotonation of compound 129 with NaH followed by reaction of the so-formed anion with epoxide 7 of Scheme 1 in DMF or DMSO at elevated temperatures produces compound 130. The nitrogen protecting group of 130, e.g., SEM is removed by treatment with, for example, 6NHCl in methanol at ambient temperatures for 3 hr to produce compound 119. Compound 119 is treated with NaH and DMSO at 20° C. for ¾ hr. and thereafter alkylated with R$_1$X to produce compound 131. In R$_1$X, R$_1$ is a C$_3$–C$_8$ alkyl group having at least one protected hydroxy moiety, e.g., O-SEM and X' is a leaving group, for example, brosylate. Removal of the hydroxy protecting group from compound 131, e.g., O-SEM is accomplished by, for example, 6NHCl in methanol to give compounds of this invention of formula I.

Scheme IIB provides an alternative, stereoselective route for preparation of the preferred compounds of this invention. Compound 135 (e.g. S-lactic acid methylester) is contacted with excess pyrrolidine in methylene chloride for 24 hours at room temperature to give amide 136. Reaction of 136 and NaH with for example, benzyl halide in DMF gave 137. Selective reduction of amide 137 with a 3.4M solution of sodium bis(2-methoxyethoxy)aluminum hydride ("RED-Al") in toluene at −20° C. gave aldehyde 138. Reaction of aldehyde 138 with H$_2$NNHCHO in methanol gave 139 which was reacted with a Grignard reagent e.g. ethylmagnesium bromide in dry ether at a temperature of −10° C. to room temperature for 24 hours to give 140 wherein the ratio of the S,S isomer: S,R isomer was 94:6. When the Grigand reaction was done in the presence of 1.2 equivalents of bis(trimethylsilyl)acetamide the SS to SR ratio was 99:1. Compound 140 was reacted with compound 13F of Scheme II in toluene in the presence of DBU (1,8-diazabicyclo [5.4.0]undec-7-ene) for six hours at 80° C. Cyclization was effected by raising the temperature to 100°–110° C. and continuing to maintain this temperature overnight. After purification via TLC, 20F was obtained. Treatment of 20F with hydrogen and palladium black in methanol containing formic acid heated to 60° C. gave the crude product which was isolated and purified (via TLC) to give compound 20F i.e. the compound of formula III wherein

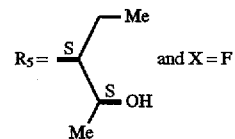

The reaction of the Grignard reagent on the propanimine 139 produces 140 wherein the absolute stereochemistry induced at the new chiral center in 140 is substantially the same (i.e., S) as that at the chiral carbon in 139. By the term "substantially the same" as used herein is meant the ratio of S:S to S:R (in e.g., 140) is greater than 9:1, preferably is greater than 15:1 and most preferably is at least 99:1.

Scheme III provides a general method for preparation of the polyether esters of alcohols of the present invention. The alcoholate of alcohol ether 21a e.g. CH$_3$(OCH$_2$CH$_2$)$_3$OH i.e., 21a wherein R$_7$=H, R$_8$=CH$_3$ and t=3, was prepared by reaction, of 21a with excess strong base e.g. NaH in an anhydrous ether e.g. THF at ice bath temperatures. The so-formed reaction mixture was stirred for several hours i.e., 2 or more and the sodium salt of acid 21b, e.g. sodium salt of chloroacetic acid (21b wherein LG=Cl, R$_7$=H and s=1) was added thereto. The so-formed reaction mixture was stirred at ice-bath temperatures and stirring was continued as temperature was allowed to warm to room temperature. Water was carefully added to the reaction mixture and the polyether acid 21c was separated and purified by conventional techniques. To a solution of 21c in CH$_2$Cl$_2$ was added 1.3–1.5 equivalents of the base 4-(N,N-dimethylamino) pyridine ("DMAP") and 20F wherein

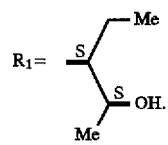

The temperature of the so formed reaction mixture was lowered by use of an ice bath and 1.3–1.5 equivalents of dicyclohexylcarbodiimide ("DCCD") was added thereto. The so-formed reaction mixture was continuously stirred as the temperature was allowed to warm to room temperature. The dicyclohexyl urea precipitate was removed and the crude product isolated by conventional techniques. The so formed residue was purified by chromatography on silica gel to provide the compound 22.

SCHEME I
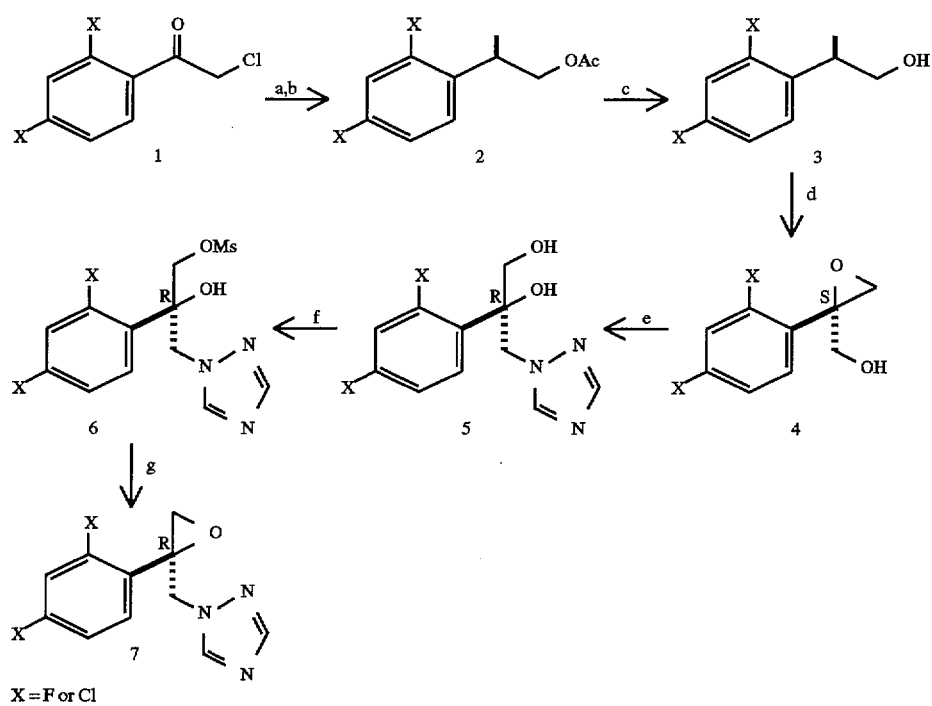
X = F or Cl
Reagents: (a) NaOAc; (b) Wittig Reaction; (c) KOH; (d) L-DET, TBHP, (i-Pr)₄Ti; (e) NaH, 1,2,4-triazole,DMF; (f) MsCl, Et₃N, CH₂Cl₂, 0–5° C.; (g) NaH,DMF.
SCHEME II
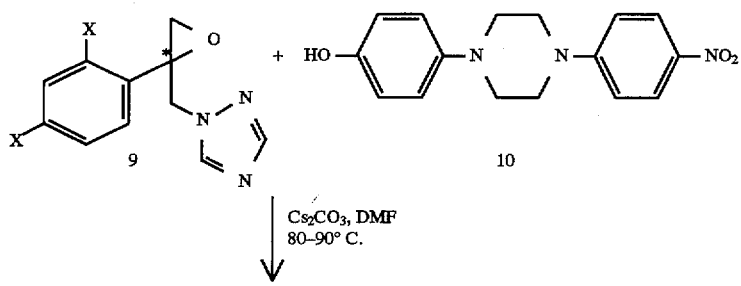
$Cs_2CO_3$, DMF
80–90° C.

-continued
SCHEME II
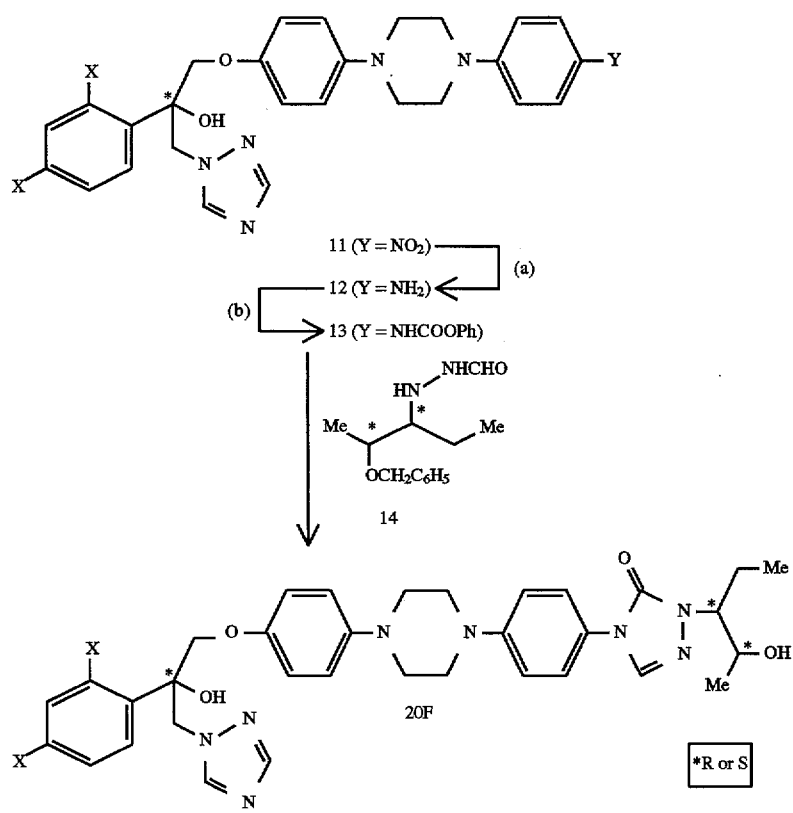
Reagents: (a) H₂, 5% Pd-C, HOAc (1 atmos.); (b) PhOCOCl, Et₃N, 0–5° C.;
(c) toluene, 80°–110° C.; (d) H₂, Pd, HCOOH, 80° C.
SCHEME IIA
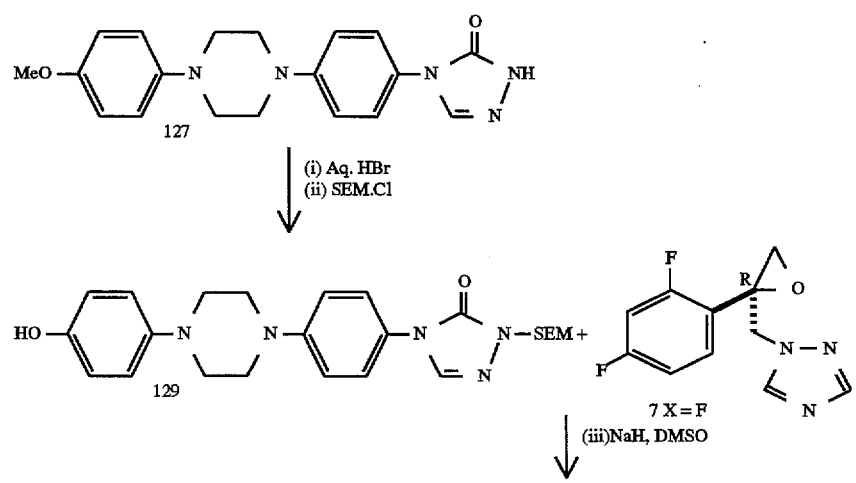

-continued
SCHEME IIA
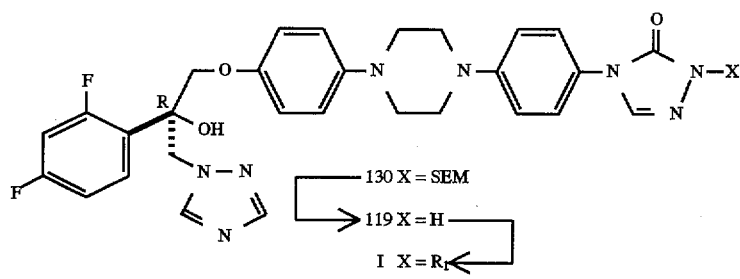
SCHEME IIB
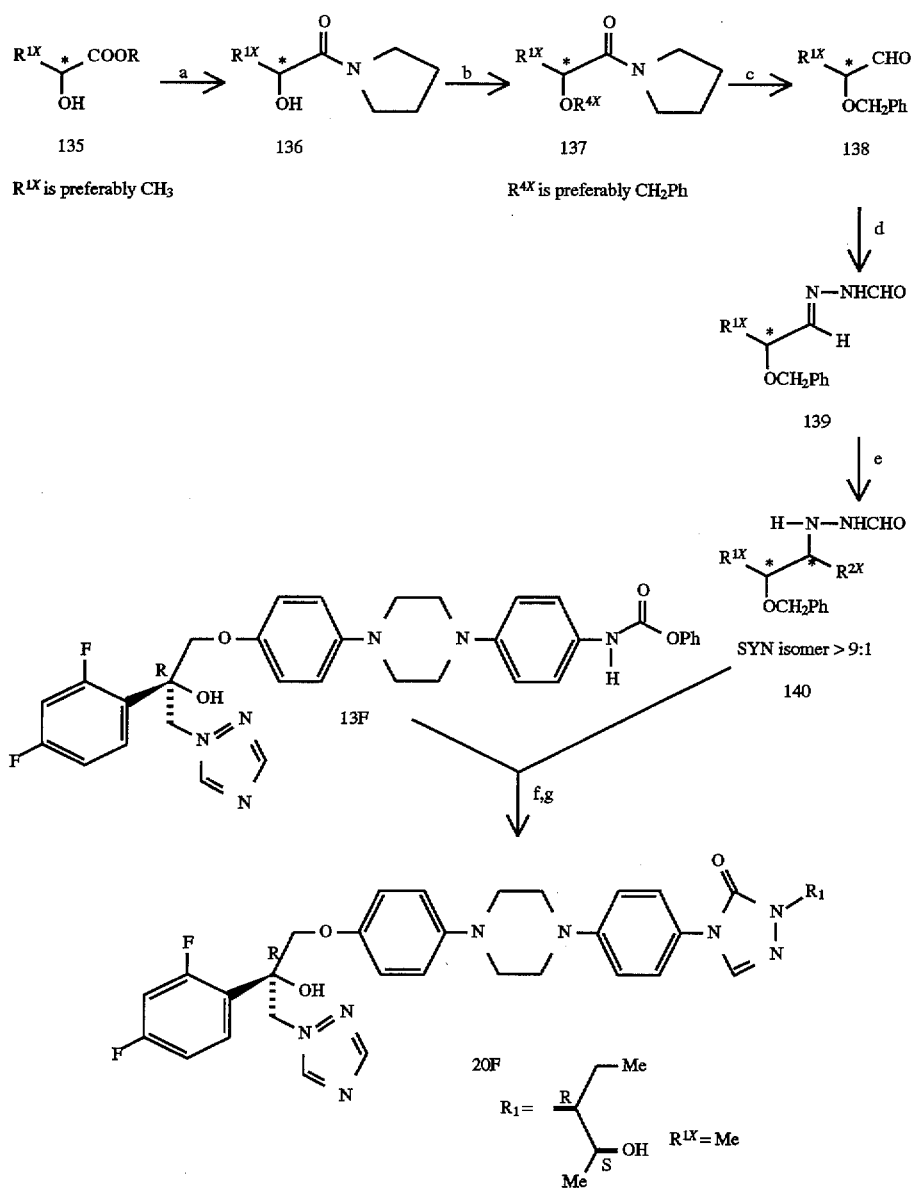

-continued
SCHEME IIB (a) pyrrolidine, r.t., 24 h; (b) $R^{4X}$—X, NaH, DMF; (c) RED-AL, toluene. $-20°$;
(d) $H_2NNHCHO$, MeOH; (e) $R^{2X}MgBr$, $Et_2O$, $-10°$ C. to r.t., 24 h; (f) 13F of
Scheme II and procedure of Example 25d; (g) $H_2$, Pd, HCOOH, 80° C.

SCHEME III $$R_8(OCHR_7CHR_7)_rOH \xrightarrow[\text{Base/THF}]{\text{LG-(CHR}_7\text{)}_s\text{CO}_2\text{Na} \atop (21b)} R_8(OCHR_7CHR_7)_t\text{—O—}(CHR_7)_s\text{—CO}_2H$$
21a                                                                              21c

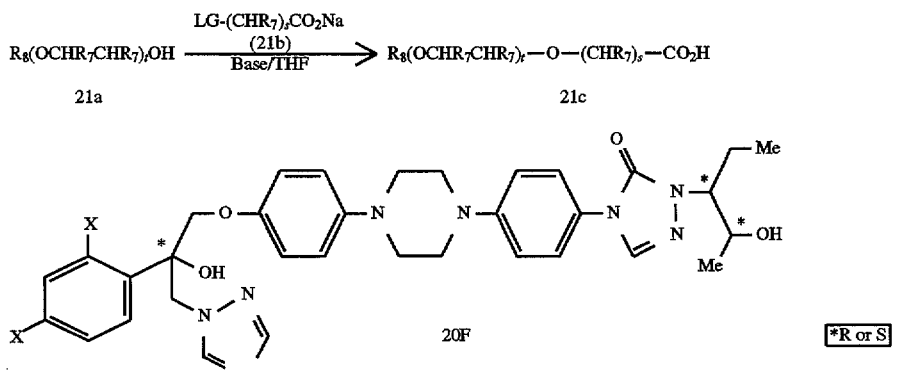

20F    [*R or S]

↓ DCCD, DMAP, HO—(CH$_2$)$_s$O(CHR$_7$CHR$_7$O)$_r$R$_8$, CH$_2$Cl$_2$
                              ‖
                              O
                             21c

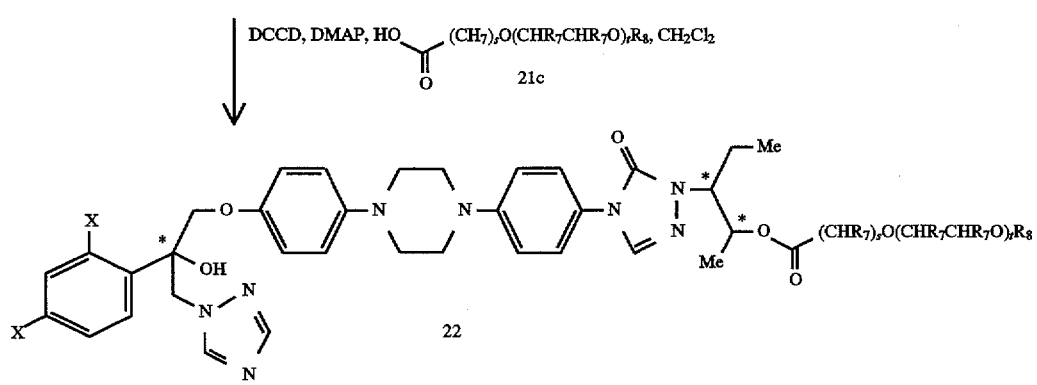

22

SCHEME IV

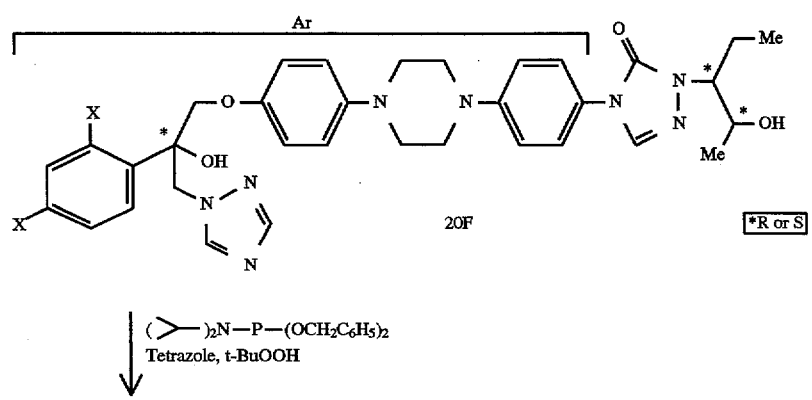

20F    [*R or S]

↓ (▷—)$_2$N—P—(OCH$_2$C$_6$H$_5$)$_2$
  Tetrazole, t-BuOOH

-continued
SCHEME IV
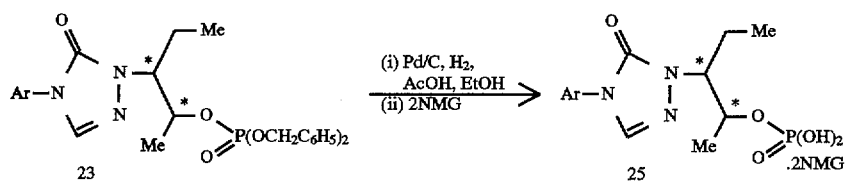
SCHEME V
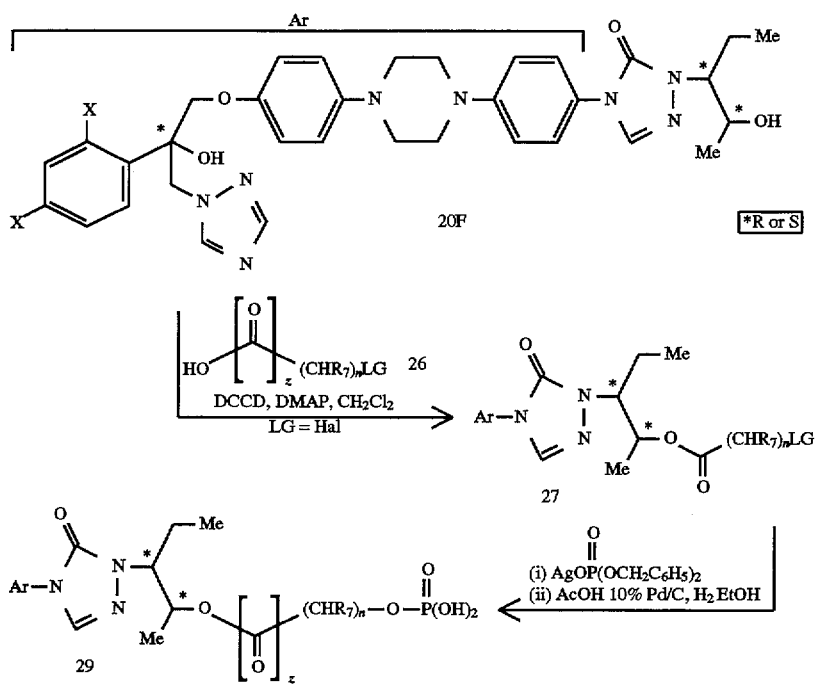
SCHEME VI
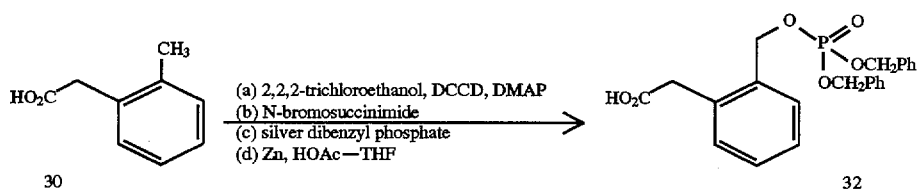

-continued
SCHEME VI
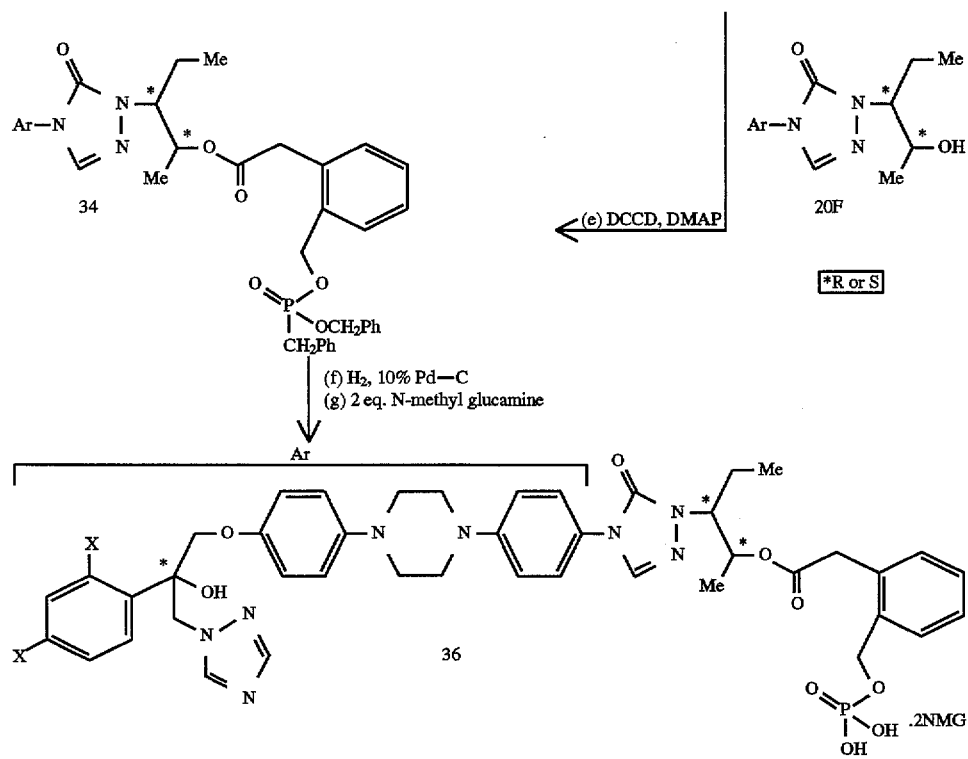
SCHEME VII
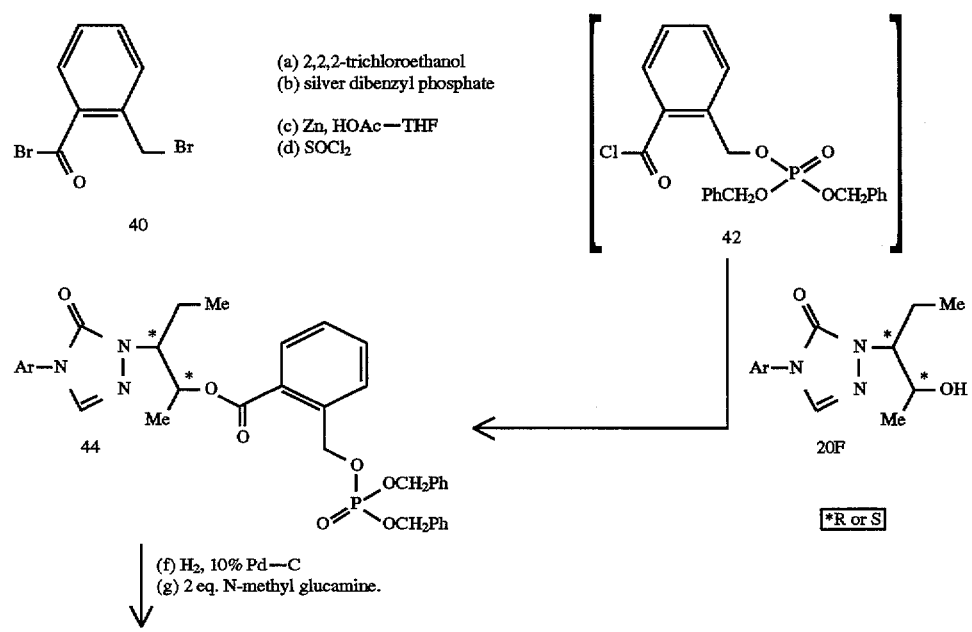

-continued
SCHEME VII
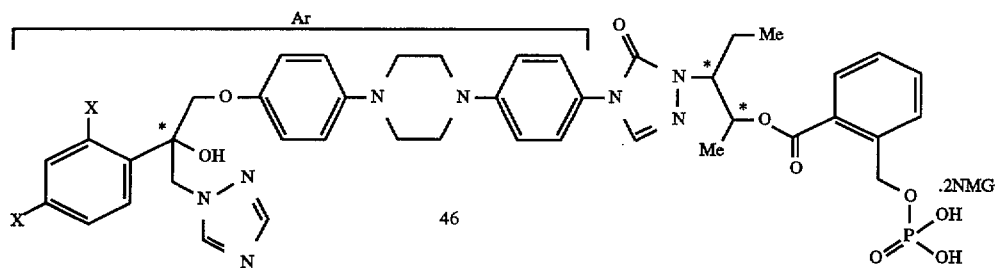
46
SCHEME VIII
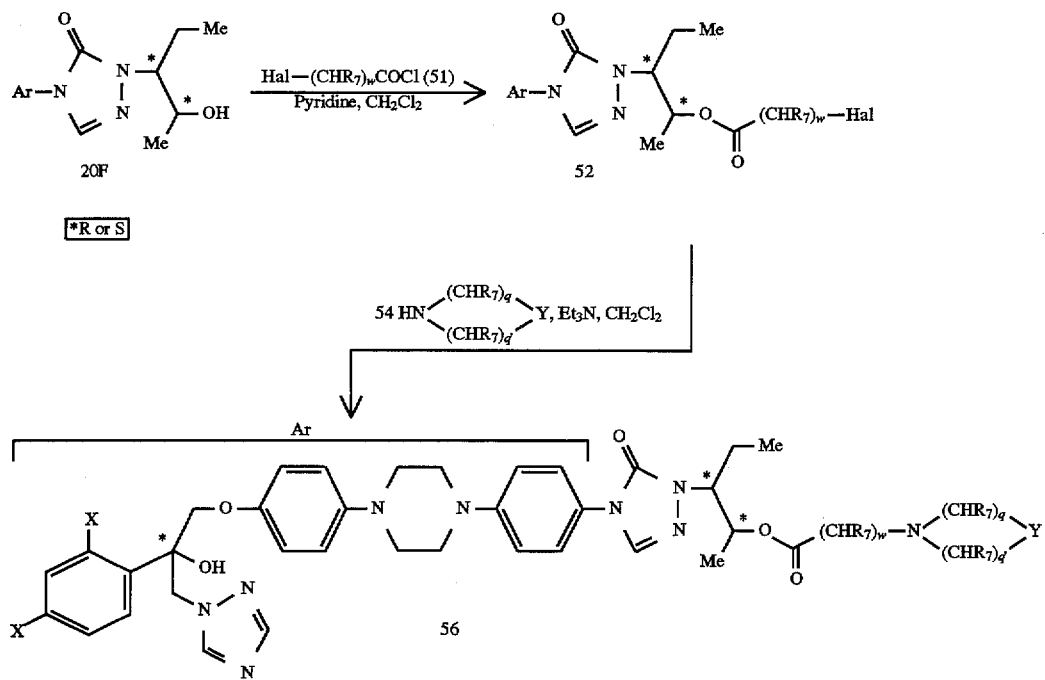
*R or S

Scheme IX

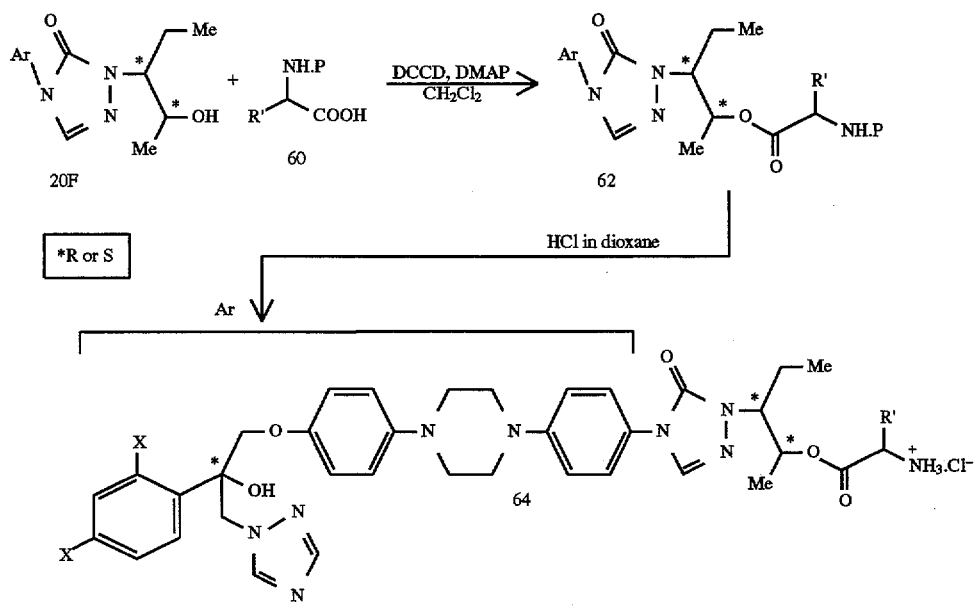

*R or S

Where
R'=H, CH$_3$, CH$_2$O H, CH(OH)CH$_3$, CH$_2$SH, CH$_2$CONH$_2$, CH$_2$CH$_2$CONH$_2$, CH(CH$_3$)$_2$, CH(CH$_3$) CH$_2$CH$_3$, CH$_2$CH$_2$SMe, CH$_2$COO$^-$, CH$_2$CH$_2$COO$^-$, (CH$_2$)$_4$NH$_3$$^+$,

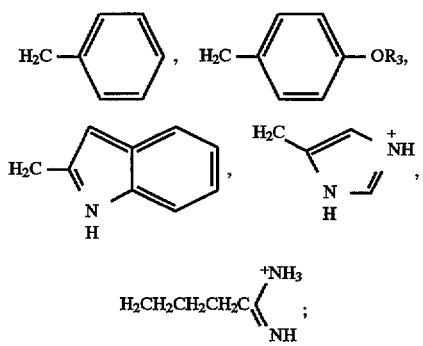

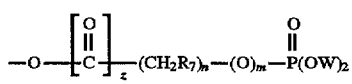

R$_3$=H, Phosphate ester, Sulphate ester; and P=N-tert-butoxycarbonyl (N-t-Boc) or N-carbobenzyloxy (N-Cbz).

Schemes IV–VII illustrate the generalised methods for preparing phosphate esters of the alcohols of this invention. Scheme IV provides a method for preparation of phosphate esters of formula IV wherein R$_6$ is $$-O-\left[\begin{matrix}O\\\|\\C\end{matrix}\right]_z-(CH_2R_7)_n-(O)_m-P(OW)_2$$

and z=m=n=0. Compound 20F of Scheme II in methylene chloride at room temperature was reacted with 1.5 equivalents of N,N-diisopropyl-dibenzylphosphoramide, and 3 equivalents of a base such as tetrazole, followed by 1.5 equivalents of tert-butyl peroxide (3M in iso-octane) for several hours. The progress of the reaction was followed by TLC (5% methanol:EtOAc v:v) on silica gel. The crude product in EtOAc was washed with sodium thiosulfate and purified using standard techniques to provide the dibenzyl phosphate ester 23. The dibenzyl ester groups of 23 were removed to give 25 by treatment of 23 dissolved in equal volumes of ethanol and glacial acetic acid in the presence of 10% Pd/C under a hydrogen atmosphere at room temperature in a stirred reactor overnight. The reaction was continued until no starting material was found by TLC (or NMR). The catalyst was removed by filtration and the crude phosphate ester 25 was purified by standard techniques. Treatment of 25 in methanol at room temperature with two equivalents of base e.g. NMG (or Et$_3$N) provided 25.2NMG.

Scheme V illustrates preparation of phosphate esters of formula IV wherein R$_6$=

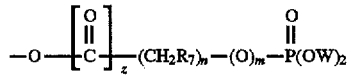

z=m=1 and n=0. Compound 20F dissolved in methylene chloride was treated with 1.3 equivalents of DMAD 1.3 equivalents of DCCD and 1.3 equivalents of the acid 26 of the formula

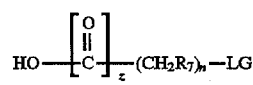

e.g., HO$_2$C(CH$_2$)$_4$Br, i.e., z=1, n=4, R$_7$=H and the leaving group LG is Br. The reaction was stirred at room temperature until no starting material was found by TLC purification of the crude product gave bromide 27, a white solid wherein

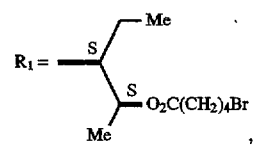

The bromide 27 in benzene was heated at 80° C. overnight with 1.5 equivalents of silver dibenzylphosphate (available from Sigma Chemical Co., St. Louis). The reaction mixture was cooled and washed with aqueous base, e.g., K₂CO₃. The crude product was separated and purified by silica gel column chromatography to give the dibenzyl phosphate ester 28. Treatment of 28 in ethanol/glacial acetic acid with 10% Pd/C under a hydrogen atmosphere overnight at room temperature gave phosphate ester 29. Treatment of 29 in methanol with two equivalents of base e.g. NMG (or Et₃N) gave 29.2NMG.

Schemes VI and VII illustrate the preparation of additional phosphate esters of this invention of the formula

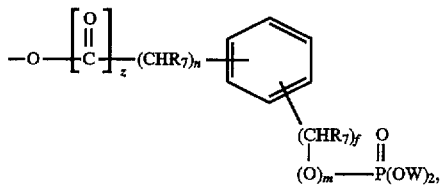

wherein z=f=m=1 n=0 or 1, and W=H.

In Scheme VI, the 2-methylphenylacatic acid 30 was esterified with 2, 2, 2-trichloroethanol and the so-formed ester was converted into corresponding the benzyl bromide by treatment with N-bromosuccinimide. The treatment of the benzyl bromide with excess silver dibenzyl phosphate under conditions of Scheme V provided the corresponding dibenzyl phosphate ester. Removal of the trichloroethyl ester group was accomplished with zinc in acetic acid-THF to give dibenzyl phosphate 32. Treatment of a solution of 32 and 20F (wherein R₁ is the same as in Scheme IV) with DCCD and DMAP provided the corresponding phosphate ester. Treatment of the phosphate ester with two equivalents of NMG gave compound 36.

In Scheme VII, the benzoyl bromide 40 is treated with 2,2,2-trichloroethanol to produce the corresponding trichloroethyl ester. Treatment of the trichloroethyl ester with excess silver dibenzyl phosphate under conditions similar to those used in Scheme V converted the benzyl bromide into a dibenzyl phosphate ester. Removal of the trichloroethyl ester group was accomplished by use of zinc in acetic acid-THF to give the dibenzyl phosphate ester 41 Treatment of 41 with thionyl chloride gave the corresponding acid chloride 42 which was contacted with a solution of 20F in methylene chloride under conditions of step one in Scheme V to give ester 44. Removal of the dibenzyl ester groups of 44 with 10% Pd/C under a hydrogen atmosphere as described in Scheme IV produced the corresponding phosphate ester which was treated with two equivalents of base e.g. NMG to provide 46.

Scheme VIII illustrates the preparation of heterocyclic esters of the present invention. Compound 20F, wherein

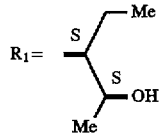

dissolved in methylene chloride is reacted with compound 51 in the (Hal=Br or Cl, w=1–5, e.g., Cl—CH₂—COCl) in presence of a base such as pyridine at a temperature of 0° –5° C. for four hours. The reaction was placed in a refrigerator overnight. Additional compound 51 and base could be added, if necessary, end the reaction continued until no 20F is present by TLC. Purification of the crude product by column chromatography on silica gel gives pure 52 (w=1, Hal=Cl). Reaction of 52 with excess of the nitrogen hetero-cyclic compound 54 (e.g., Y=NH, R₇=H and q+q'-=4) at a temperature of 50°–60° C. for 1 hour produces 36. Substitution of nitrogen heterocyclic compound 54 with a five and six membered compounds, e.g. morpholine, N-methylpiperidine provides the corresponding heterocyclic compounds.

Scheme IX illustrates preparation of the amino acid ester derivatives of the compounds of this invention. Compound 20F is contacted with excess N-(-butoxy carbonyl α-amino acid or α-amino alkanoate 60 in the presence of DCCD and DMAP in an aprotic solvent such as CH₂Cl₂ at 0° to 25° C. The reaction is followed by TLC and additional α-amino acid and DCCD are added, if necessary, to insure the starting material 20F is completely converted into protected amino acid ester derivative 62. Compound 62 is treated HCl in dioxane to provide the α-amino acid ester as the acid addition salt 64. Purification of the crude products is accomplished by standard techniques. When carbobenzoxy is used as the protecting group, hydrogen over palladium black in the presence of an acid (eg. HCl or HCOOH) is used to remove the protecting group such that the α-amino acid ester is obtained as the acid addition salt 64. Other protecting groups may be used such as those disclosed in "Protective Groups in Organic Synthesis" by T. W. Green and P. G. M. Wuts. John Wiley and Sons 1991 NY at pages 97–98 or 389–394.

The alkanoate and alkenoate esters of 20F are conveniently prepared by standard synthetic techniques, (for example, by reaction of the anhydride or acid halide of the alkanoic acid or alkenoic acid in the presence of base e.g, pyridine) produced the alkanoate or alkenoates of the compounds of formula I.

The sulfate esters may be prepared by reaction of the alcohol compounds of formulas I to IV with sulfur trioxide in the presence of excess pryridine at temperatures of 70°–90° C. for at least 2 hours in accordance with the procedure of R. M. Moriarty et. al., *Tetrahedron Letters*, Vol. 35, No. 44, p 8103–8106 (1994).

The compounds of formula I may also be prepared by reaction of compound 9 with alcohols of formula HOQ in the presence of a strong base, e.g., NaH in an aprotic solvent, such as DMSO.

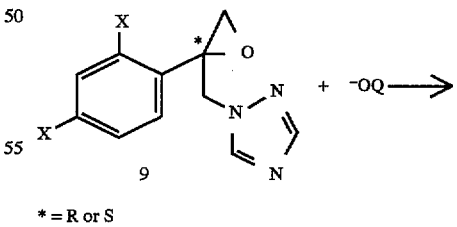

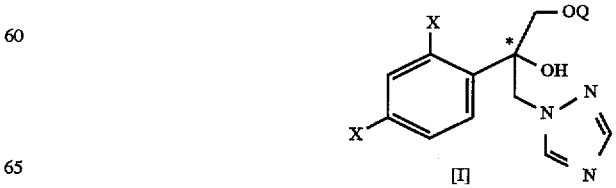

See Examples 12–25
wherein
X=F or Cl

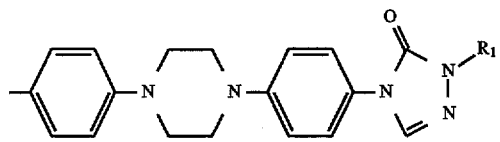

and R₁=a (C₃–C₈) alkyl group substituted by one or two hydroxy moieties. The use of compound 9 (*=the R absolute configuration, i.e. compound 7 of Scheme I) is preferred.

Compounds represented by formula I exhibit broad spectrum antifungal activity, in conventional antifungal screening tests, against human and animal pathogens, such as the following: Aspergillus, Blastomyces, Candida, Cryptococcus, Coccidioides, Epidermophyton, Fonsecaea, Fusarium, Mucor, Saccharomyces, Torulopsis, Trichophyton, Trichosporon, Sporothrix and Pneumocystis.

The antifungal compounds of formula I and pharmaceutical compositions of this invention are expected to exhibit anti-allergic, anti-inflammatory and immunomodulating activities, broad spectrum antiinfective activity, e.g., antibacterial, anti-protozoal and antihelminthic activities.

The present invention also provides a composition for treating or preventing fungal infections comprising an antifungally effective amount of a compound represented by formula I or a pharmaceutically acceptable salt thereof and a pharmaceutically acceptable carrier or diluent therefor.

The pharmaceutical compositions of the present invention may also contain a fungicidally effective amount of other antifungal compounds such as cell wall active compound. The term "cell wall active compound", as used herein, means any compound that interferes with the fungal cell wall and includes, but is not limited to, compounds such as papulacandins, echinocandins, and aculeacins as well as fungal cell wall inhibitors such as nikkomycins, e.g, nikkomycin K and others which are described in U.S. Pat. No. 5,006,513 which is hereby incorporated by reference.

The pharmaceutically acceptable salts of the compounds of the present invention include pharmaceutically acceptable acid and base addition salts.

The preferred pharmaceutically acceptable acid addition salts are nontoxic acid addition salts formed by adding to the compounds of the present invention about a calculated amount of a mineral acid, such as HCl, HBr, $H_2SO_4$, $HNO_3$ or $H_3PO_4$, or of an organic acid, such as an alkyl or arylsulfonic acid such as methanesulfonic, para-toluenesulfonic, naphthylsulfonic and the like.

The pharmaceutically acceptable bases found suitable for use in the present invention are those which form pharmaceutically acceptable salts of the acidic pharmaceutically acceptable esters of the antifungal compounds of formulas I, II, III or IV and include suitable organic and inorganic bases. Suitable organic bases include primary, secondary and tertiary alkyl amines, alkanolamines, aromatic amines, alkylaromatic amines and cyclic amines. Exemplary organic amines include the pharmaceutically acceptable bases selected form chloroprocaine, procaine, piperazine, glucamine, N-methylglucamine, N-N-dimethyl glucamine ethylendediamine, diethanolamine, diisopropylamine, diethylamine, N-benzylenediamine, diethanolamine, diisopropylamine, diethylamine, N-benzyl-2-phenylethylamine, N-N'dibenzylethylenediamine, choline, triethylamine ("ET₃N"), tris(hydroxymethyl) aminomethane, or D-glucosamine. The preferred organic bases include N-methyl glueamine ("NMG"), diethanolamine, and tris(hydroxymethyl) aminomethane ("TRIS"). Use of two equivalents of NMG in this invention is more preferred. The suitable inorganic bases also include alkali metal hydroxides such as sodium hydroxide.

The pharmaceutical compositions of the present invention may be adapted for any mode of administration e.g., for oral, parenteral, e.g., SC, IM. IV and IP, topical or vaginal administration or by inhalation (orally or intranasally) Such compositions are formulated by combining the compound of formula I or an equivalent amount of a pharmaceutically acceptable salt of compound I with an suitable, inert, pharmaceutically acceptable carrier or diluent.

Examples of suitable compositions include solid or liquid compositions for oral administration such as tablets, capsules, pills, powders, granules, solutions, suppositories, troches, lozenges, suspensions or emulsions. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet, the active compound is mixed with carrier having the necessary binding properties in suitable proportions and compacted in the shape and size desired.

Topical dosage forms may be prepared according to procedures well known in the art, and may contain a variety of ingredients, excipients and additives. The formulations for topical use include ointments, creams, lotions, powders, aerosols, pessaries and sprays.

For preparing suppositories, a low melting wax such as a mixture of fatty acid glycerides or cocoa butter is first melted, and the active ingredients are dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution with an appropriate amount of a hydroxypropyl α- β or -γ-cyclodextrin having 2 to 11 hydroxypropyl groups per molecule of cyclodextrin, polyethylene glycol, e.g., PEG-200 or propylene glycol, which solutions may also contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water. A particularly preferred aqueous pharmaceutical composition may be prepared from the compounds of formulas I to IV together with hydroxypropyl-β-cyclodextrin in water. The use of derivatives of α-, β- and γ-cyclodextrins, for example, hydroxpropyl-β-cyclodextrin are disclosed by N. Bodor U.S. Pat. No. 4,983,586, Pitha U.S. Pat. No. 4,727,064 and Janssen Pharmaceutical International Patent Application No. PCT/EP 84/00417.

The pharmaceutical compositions of the present invention may be prepared by admixing the pharmaceutically acceptable carrier, e.g., a hydroxypropyl-β-cyclodextrin in water, and adding thereto an antifungally effective amount of a drug of the present invention. The solution so formed is filtered, and optionally, the water may be removed by well known methods, e.g., rotatory evaporation or lyophilization. The formation of the solution may take place at a temperature of about 15° to 35° C. The water is normally sterilized water and may also contain pharmaceutically acceptable salts and buffers, e.g., phosphate or citrate as well as preservatives. The molar ratio of the antifungal compound of formula I to hydroxpropyl-β-cyclodextrin is about 1:1 to 1:80, preferably 1:1 to 1:2. Normally the hydroxypropyl-β-cyclodextrin is present in molar excess.

Also included are solid form preparations which are intended to be converted, shortly before use, into liquid form preparations for either oral or parenteral administration. The solid form preparations intended to be converted to liquid form may contain, in addition, to the active materials, such as compounds of this invention, and optionally a cell wall active compound, especially a fungal cell wall inhibitor, e.g., a nikkomycin, flavorants, colorants, stabilizers, buffers, artificial and natural sweeteners, dispersants, thickeners, solubilizing agents and the like. The solvent utilized for preparing the liquid form preparations may be water, isotonic water, ethanol, glycerin, polyethylene glycols, propylene glycol, and the like, as well as mixtures thereof.

Parenteral forms to be injected intravenously, intramuscularly, or subcutaneously are usually in the form of a sterile solution, and may contain salts or glucose to make the solution isotonic.

The topical dosage for humans for antifungal use in the form of a pharmaceutical formulation comprising a compound of formula I (usually in the concentration in the range from about 0.1% to about 20% preferably from about 0.5% to about 10% by weight) together with a non-toxic, pharmaceutically acceptable topical carrier, is applied daily to the affected skin until the condition has improved.

In general, the oral dosage for humans for antifungal use ranges from about 1 mg per kilogram of body weight to about 50 mg per kilogram of body weight per day, in single or divided doses, with about 1 mg per kilogram of body weight to about 30 mg per kilogram of body weight per day being preferred and the dose of about 1 mg per kilogram of body weight to about 20 mg per kilogram of body weight per day being most preferred.

In general, the parenteral dosage for humans for antifungal use ranges from about 0.25 mg per kilogram of body weight per day to about 30 mg kilogram of body weight per day, in single or divided doses, with about 0.5 to about 20 mg per kilogram of body weight per day being preferred.

The exact amount, frequency and period of administration of the compounds of the present invention for antifungal use will vary, of course, depending upon the sex, age and medical condition of the patient as well as the severity of the infection as determined by the attending clinician.

GENERAL EXPERIMENTAL

The compounds of this invention are prepared in accordance with Schemes I–IX hereinabove and the following Examples using commercially available starting materials.

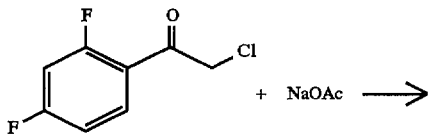

+ NaOAc ⟶

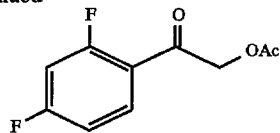

EXAMPLE 1a

2-Acetyloxy-1(2,4-difluorophenyl)ethanone

Add 191 g of 2-chloro-2',4'-difluoroacetophenone (Aldrich Chemical Co.) to a mixture of 246 g of sodium acetate, 3 g of NaI, and 3 L of DMF. Stir the mixture at 20° C. for 18 hr. then concentrate it to 1 L. Pour the residue into 6 L of cold dilute aqueous HCl and extract with EtOAc. Wash the extract with brine, dry it over anhydrous Na₂SO₄, filter the so-formed mixture, and evaporate the filtrate to leave a residue. Chromatograph the residue on silica gel, eluting with CH₂Cl₂-hexane to obtain 198 g of the title compound.

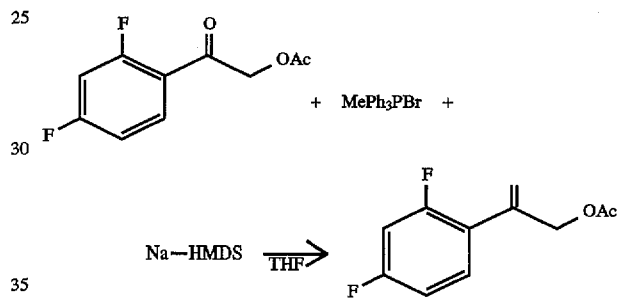

EXAMPLE 1b

1-[2-(2,4-Difluorophenyl)]-2-propenol acetate

Suspend 131 g of MePh₃PBr in 270 mL of mechanically-stirred, dry THF at 20° C. Add 393 mL of 1M NaN(Me₃Si)₂ in THF, slowly at first, then rapidly over 5 min. while applying just enough ice cooling to maintain the temperature at <23° C. Stir the so-formed mixture for 1 hr at 20°–24° C., cool it to ~70° C., and stir it another ½ hr. Then add thereto a solution of 65.5 g of the product of Example 1a in 140 mL of dry THF, at a rate slow enough to keep the temperature below −70° C. Continue to stir the so-formed reaction mixture in the cold bath overnight during which the temperature rises to 20° C. Add 50 mL of EtOAc to the so-formed suspension, and then add 3 L of hexane. Allow the so-formed mixture to stand for ~15 min., and suction-filter to remove Ph₃PO. While the filter cake is still damp, transfer it to a beaker. Triturate the cake thoroughly with 1/2 L of hexane and suction-filter again to remove the remainder of product. Wash the combined hexane filtrates with 2×1 L of a 1:1 (v/v) MeOH-water, and then with brine. Dry the organic layer over MgSO₄, filter and evaporate the filtrate to leave a red oil. Add 1.5 L of hexane and suction-filter through a Celite pad to leave a clear yellow solution. Chromatograph the yellow oil on silica gel, eluting with 1/2 L of hexane, then 1L of 15:1 (v/v) hexane-EtOAc. Combine the homogeneous fractions to yield 38.6 g of the title compound as an oil.

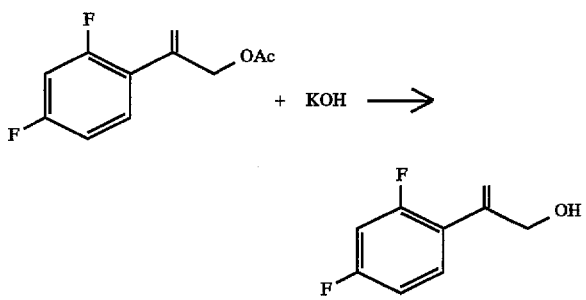

EXAMPLE 1c

2(2,4-Difluorophenyl)-2-propenol

Dissolve 40 g of the product of Example 1b in 400 mL of dioxane. Add a solution of 18 g of 85% KOH in 315 mL of water. Stir the so-formed mixture vigorously for 1 hr, and then pour the mixture into 1 L of $Et_2O$. Separate the aqueous layer and extract it with 250 mL of $Et_2O$. Combine the organic extracts, and wash them with water and then brine. Dry the organic extract over anhydrous $K_2CO_3$, and add 10 g of charcoal thereto. Filter, and evaporate the filtrate to leave 31.3 g of the title compound as a straw-colored oil.

EXAMPLE 1d

(S)-(−)-[2-[2-(2,4-Difluorophenyl)]oxiranyl] methanol

Add 33 g of activated 3 Å molecular sieve powder to a solution of 13 g of L-(+)-diethyl tartarate in 2.3 L of $CH_2Cl_2$, and cool the so-formed mixture to −5° C. Add a solution of 15.4 mL of titanium tetra-isopropoxide in 100 mL of $CH_2Cl_2$ over 2–3 minutes and then cool the so-formed mixture to −22° C. Add 109.5 mL of a 5.5M solution of tert-butylhydroperoxide in 2,2,4-trimethylpentane over 4–6 minutes, and cool the so-formed mixture to −25° C. Stir the mixture at −25° C. for 25 minutes and then add a solution of 40 g of 2-(2,4-difluorophenyl)-3-propenol of Example 1c in 100 mL of $CH_2Cl_2$ over 3–4 minutes. Stir the so-formed mixture at −27° C. for 4½ hour. Add 102 mL of 30% aqueous sodium hydroxide saturated with NaCl and stir the so-formed mixture while warming to +10° C. over a ½ hour period. Add thereto 100 g of anhydrous $MgSO_4$ and 33 g of Celite, and stir ½ hour at +10° C. Suction-filter the mixture, wash the so-formed filter cake with 1.2 L of diethyl ether ($Et_2O$) and then 1.5 L of toluene, and dry the combined organic layers over anhydrous $MgSO_4$. Filter the organic layer, and evaporate the filtrate in vacuo to form a residue. Dissolve the residue in 1 L of $Et_2O$ and suction-filter the mixture to remove insolubles. Suction-filter the filtrate through 100 g of silica gel, and wash the pad with 200 mL of fresh $Et_2O$. Evaporate the filtrate in vacuo to give 41 g (94%) of the crude title compound as a yellowish oil, $[\alpha]_D^{25}$−36.7° (c=I, MeOH); PMR ($CDCl_3$) δ7.40(m,1H), 6.85(m,2H), 3.95(m,2H), 3.31(d,1H), 2.84 (d,1H), 1.91(m, 1H, deuterium exchangeable).

EXAMPLE 2

(R)-(+)-[2-[2-(2,4-Difluorophenyl)]oxiranyl] methanol

Follow the procedure of Example 1d, except substitute an equivalent amount of D-(−) diethyl tartarate in place of L-(+) diethyl tartarate to give the crude title compound, $[\alpha]_D^{25}$+33.9° (c=I, MeOH).

Purify a portion of the crude compound by silica gel chromatography to obtain a sample homogeneous by TLC, $[\alpha]_D^{25}$+40.0° (c=I, MeOH)

EXAMPLE 3

(R)-(−)-2-(2,4-Difluorophenyl)-3-(1,2,4-triazol-1-yl)-1,2-propanediol

Dissolve 8.91 g of 1H-1,2,4-triazole in 150 mL of anhydrous DMF and cool so-formed mixture to 0°–5° C. Add 2.81 g of sodium hydride (60% oil dispersion) and stir the so-formed mixture 30 minutes at room temperature. Add thereto 10.9 g of the product of Example 1d. Stir the so-formed reaction mixture for 2 hours at 60°–70° C. Cool the mixture to room temperature, add thereto 10 ml of $H_2O$ and evaporate it in vacuo to give a residue. Dissolve the residue in 100 mL of $H_2O$ and 900 ml of ethyl acetate (EtOAc). Extract the $H_2O$ layer with another 250 mL of EtOAc. Wash the combined EtOAc extracts with 100 mL of brine. Dry the EtOAc extracts over anhydrous $MgSO_4$ and evaporate. Triturate the so-formed oily residue with 10 mL of $CH_2Cl_2$ and add 100 mL of $Et_2O$. Stir the $CH_2Cl_2$—$Et_2O$ mixture for 1 hour at room temperature. Filter to give 11.2 g (75%) of the title compound, $[\alpha]_D^{25}$−70.7 (c=1.0, MeOH), mass spectrum (FAB): 256 [M+H]$^+$. Recrystallize 1.0 g of the filtered product from 5 mL of $CH_3CN$ to give 0.83 g of the title compound, m.p. 99°–100° C.; $[\alpha]_D$−71.5° (c=1.0, MeOH); elemental analysis: Calculated for $C_{11}H_{11}F_2N_3O_2·½CH_3CN$: 52.27C, 4.57H, 17.78N, 13.78F; Found: 52.26C, 4.58H, 17.54N, 13.78F; PMR(DMSO) δ8.25 (s,1), 7.66(s,1), 7.33, (m,1), 7.09(t,1), 6.90(t,1), 5.72 (s,1), 5.05(t,1), 4.53(s,2), 3.61(m,2).

EXAMPLE 4

(S)-(+)-2(2,4-Difluorophenyl)-3-(1,2,4-triazol-1-yl)-1,2-propanediol

Follow the procedure of Example 3, except substitute an equivalent quantity of the product of Example 2 in place of the product of Example 1 to give the title compound; MP. 95°–101° C.; $[\alpha]_D^{25}$+70.0° (c=1.0, MeOH). The PMR and Mass spectra were consistent with the structure of the title compound.

EXAMPLE 5

(R)-2-(2,4-Difluorophenyl)-3-(1,2,4-triazol-1yl)-1,2-propanediol-1-methanesulfonate Suspend 10.9 g of the powdered product of Example 3 in 150 mL of $CH_2Cl_2$. Add thereto 8.95 mL of triethylamine and cool to the so-formed mixture 0°–5° C. Add 3.64 mL of methanesulfonyl chloride in 20 ml of $CH_2Cl_2$ over 10 min. Stir the so-formed mixture for 1 hour at room temperature. Cool it to 0°–5° C., extract with 100 mL of cold (0°–5° C) 5% $KH_2PO_4$, followed by 100 mL of cold (0°–5° C.) $H_2O$, followed by 50 mL of brine. Dry the separated organic layer over anhydrous $MgSO_4$ and evaporate to obtain 13.7 g (96%) of the title [M+H+]$^+$; PMR ($CDCl_3$) δ7.95 (s,1), 7.82 (s,1), 7.53(m,1), 6.81(m,2), 4.84(d,1), 4.65(d,1), 4.46(m,2), 3.05(s,3).

EXAMPLE 6

(S)-2(2,4-Difluorophenyl)-3-(1,2,4-triazol-1yl)-1,2-propanediol-1-methanesulfonate Follow the procedure of Example 5, except substitute an equivalent quantity of the product of Example 4 in place of the product of Example 3 to give the title compound. The PMR is consistent with the structure of the title compound.

EXAMPLE 7

(R)-1-[2-[2-[2,4-Difluorophenyl)]oxiranylmethyl]-1,2,4-triazole

Dissolve 13.7 g of the product of Example 5 in 200 mL of anhydrous DMF and cool the so-formed solution to 10°–15° C. Add thereto 1.71 g of sodium hydride (60% oil dispersion) and stir the so-formed reaction mixture at room temperature for 90 minutes. Concentrate in vacuo to 50 mL. Add thereto 200 mL of cold $H_2O$ (0°–5° C.) and extract with 3×200 mL portions of EtOAc. Wash the combined EtOAc extracts with 100 mL of brine. Dry the EtOAc extracts over anhydrous $MgSO_4$ and evaporate it to give 10.8 g of a residue. Apply the residue in $CH_2Cl_2$ to a column of 400 g of MPLC grade silican gel previously prepared by slurry packing with $CH_2Cl_2$ containing 1 mL of $Et_3N$ per liter. Elute with 1 liter, each of 25, 50 and 75% EtOAc; $CH_2Cl_2$ (v/v) followed by 2 liters of EtOAc. Combine the fractions to give 6.92 g (68%) of the title compound. Mass spectrum (FAB): 238 [M+H]+; PMR ($CDCl_3$) δ7.97(s,1), 7.77(s,1), 7.07(m,1), 6.73(m,2); 4.73(d,1), 4.41(d,1), 2.84(d,1), 2.78 (d,1).

EXAMPLE 8

(S)-1-[2-[2-(2,4-difluorophenyl)]oxiranylmethyl]-1,2,4-triazole

Follow the procedure of Example 7, except substitute an equivalent amount of the product of Example 6 in place of the product of Example 5 to give the title compound. [PMR is consistent with the structure of the title compound].

EXAMPLE 9

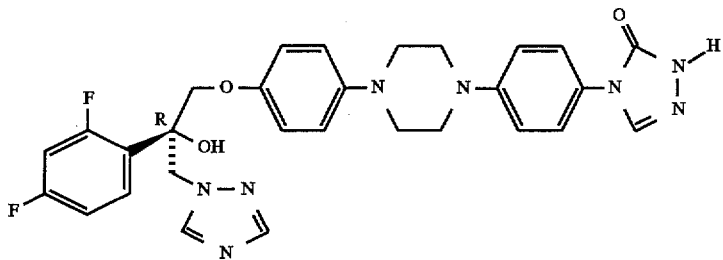

The title compound is prepared starting with the compound of Example 7 and compound 129 and using the synthetic scheme outlined in Scheme IIA.

EXAMPLE 10

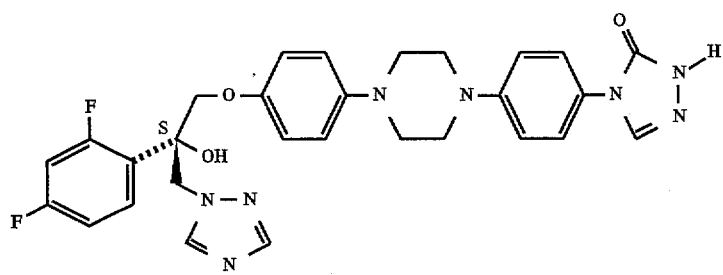

The title compound is prepared in accordance with the procedures of Example 9 except than an equivalent amount of the compound of Example 8 is substituted for the compound of Example 7.

EXAMPLE 11

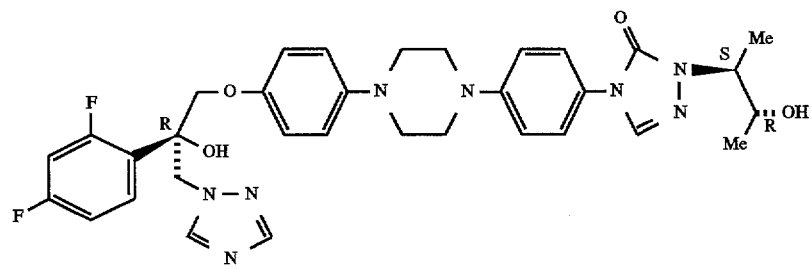

a. 2-O-SEM Ether of (2R,3R)-2,3-Butanediol

To a stirred solution of 4.95 g of (2R, 3R)-2,3-butanediol, (55 mmoles) and 9.3 g of SEM-Cl (55.7 mmoles) in 55 ml of anhydrous DMF at 0° C. were added in four portions 2.34 g of 60% oil-dispersed NaH (58.5 mmoles) over 10 min. The resulting mixture was stirred at 0° C. for 4 hours and at ambient temperature overnight. The turbid reaction mixture was poured onto 0.5 L of 5% $KH_2 PO_4$ solution and extracted with 2×300 ml of ether; the combined ethereal solution was washed once with distilled water, saturated brine, dried over $MgSO_4$ and evaporated to give a colorless liquid. Flash chromatography over 350 g silica gel with 1 L of 7% ETOAC/Hexane, 2 L of 10% ETOAC/Hexane and 1 L of 15% ETOAC/Hexane gave 1.74 g of the title compound (yield 14.4%) MS:(M+H)$^+$=221.

b. Brosylation

A mixture of 0.7 g of the 2-O-SEM ether of Example 11 (a), (3.18 mmoles) and 0.97 g of 4-bromobenzenesulfonyl chloride (3.82 mmoles) in 5 ml of anhydrous pyridine was stirred under $N_2$ atmosphere at ambient temperature for 6 hours. The reddish slurry reaction mixture was diluted with 50ml of ice-cold water, extracted with 2×25 ml of ether. The combined ethereal solution was washed with 2×25 ml of 1-% $CuSO_4$ solution, distilled water, saturated brine, dried over $MgSO_4$ and evaporated to give a reddish oily residue.

Flash chromatography over 50 g silica gel with 1 L of 10% ETOAC/Hexane gave 1.02 g of the brosylate as a colorless liquid (yield 72.9%) $[\alpha]_D^{23}=-69°$ (CHCl$_3$; c=1)

c. Alkylation Reaction

Stir a mixture of 0.98 g of the brosylate of Example 11(b) (2.23 mmoles), 0.69 g of the 3H-1,2,4-triazol-3-one of Example 9 (1.12 mmoles) and 0.37 g of cesium carbonate (1.12 mmoles) in 20 ml of anhydrous DMF at 80° C. under N$_2$ overnight (~20 hours). Dilute the reaction mixture with 100 ml of ice-cold water, extract it with 2×50 ml of ethyl acetate. Wash the combined organic solution once with distilled water, saturated brine, dry it over MgSO$_4$ and evaporate the solution to give a solid residue. Flash chromatography of the residue over 125 g silica gel with 1.2 L of 80% ETOAC/Hexane gives the product.

d. Acidic Hydrolysis of 11(c) to the title product

Stir a mixture of 0.32 g of the SEM-ether of Example 11(c) and 6 ml of 6N HCl solution in 6 ml of methanol at ambient temperature for 4 hours and evaporate it under reduced pressure. Dilute the residue with 5 ml of ice water, basify it carefully with 10% Na$_2$CO$_3$ solution until pH=8-9 is obtained. Extract the so-formed reaction mixture with 2×25 ml of CH$_2$Cl$_2$ and wash it with saturated brine, dry it over MgSO$_4$ and evaporate it to give a product. Filtration of the product through a 50 g silica gel column and elution with 0.75 L of 4% MeOH/CH$_2$Cl$_2$ gives the title product.

b. Basic Hydrolysis of the o-Nitrobenzoate

A solution of 1.12 g of of the p-nitrobenzoate of Example 12(a) (3 mmoles) and 3.5 ml of 1N NaOH solution in 20 ml of methanol was stirred at ambient temperature for 3 hours. Solvents were evaporated and the residue was diluted with 10 ml of distilled water, and extracted with 2×20 ml of ether. The combined ethereal solution was washed once with saturated brine, dried over MgSO$_4$ and evaporated to give 0.67 g of the corresponding alcohol as a colorless liquid (~100%), which was used directly for the next reaction without further purification.

c. Brosylation, Alkylation and Acidic Hydrolysis

Follow the procedures of Example 11(c) and (d), to give the title compound.

EXAMPLE 12

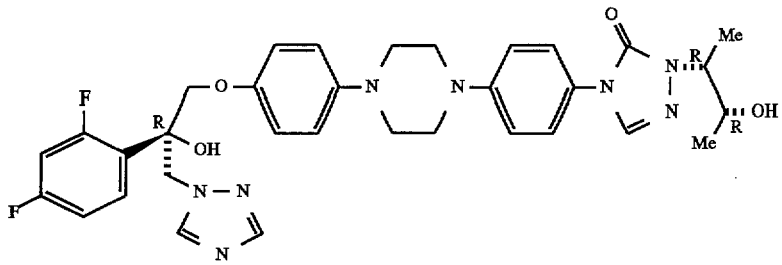

a. Mitsunobu Reaction

To a stirred solution of 0.72 g of the 2-O-SEM ether of Example 11(a) (3.27 mmoles), 2.1 g of triphenyl phosphine (8.06 g) and 1.2 g of p-nitrobenzoic acid (7.17 mmoles) in 30 ml of dry benzene at 0° C. were added, dropwise, 1.25 ml (8.06 mmoles) of diethyl azodicarboxylate ("DEAD"). The so-formed clear yellow solution became turbid and the mixture was stirred at ambient temperature for 2 hours, and mixture loaded on a 100 g silica gel column. Elution of the column with 15% ETOAC/Hexane gave 1.5 g of the 3-β-nitrobenzoate having the S absolute configuration (95% yield) MS: 219 (M$^+$–150), 252 (M$^+$–117).

EXAMPLE 13

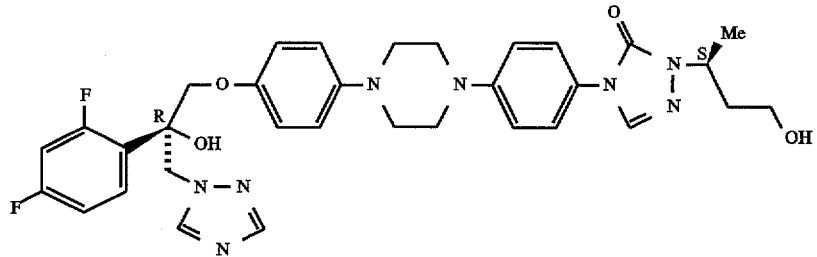

a. Formulation of TBDPS Ether

To a solution of 0.9 g or (R)-(–)-1,3-butanediol (10 mmoles), 1.5 g of imidazole (22 mmoles) in 10 ml of anhydrous DMF at 0° C. were added 3 ml of t-butylchlorodiphenylsilane ("TBDPS") (11 mmoles) over 3 minutes. The reaction mixture was stirred at 0° C. for 4 hours, diluted with 50 ml of ice-cold water and extracted with 2×30ml of ether. The aqueous phase was back extracted with 50 ml of ether and the combined ethereal solution was washed once with saturated brine, dried over MgSO$_4$ and evaporated to give a colorless residue. Flash chromatography over 150 g silica gel with 1.5 L of 5% EtOAC/Hexane and 1 L of 10% EtOAC/Hexane gave 2.87 g of the TBDPS ether (87.5%) MS: [M+H]⁺: 329; [α]$_D^{23}$=+0.64° (CHCl₃; c=1)

b. Brosylation

To a solution of 0.984 g of TBDPS ether of Example 13(a) (3 mmoles) in 7 ml of anhydrous pyridine were added 0.845 g of 4-bromobenzenesulfonyl chloride (3.3 mmoles). The reaction was run and worked-up and purified in accordance with the procedure of Example 11(b) and 1.02 g of the brosylate was obtained in 61.1% yield; MS: [M+23]⁺=569/571; [α]$_D^{23}$+2.45° (CHCl₃; c=1)

c. Alkylation

React the brosylate of Example 13(b), 0.95 g (1.74 mmoles) with the compound of Example 9 according to the procedure of Example 11(c) to provide the corresponding alkylated product.

d. Acidic Hydrolysis

Hydrolyze the compound of Example 13(c), 0.32 g, (0.35 mmoles) by 6N HCl solution in accordance with the procedure of Example 11(d) to give the title compound.

Alternatively stir a solution of 0.19 g of the compound of Example 13(c) and 60 mg of tetrabutylammonium fluoride (0.23 mmoles) in 5 ml of THF ambient temperature for 24 hours. Concentrate the solution. Flash chromatography of the concentrated solution over 50 g silica gel with 0.5 L each of 2% and 4% MeOH/CH₂Cl₂. gives of the title compound.

ml of benzyl trichloroacetimidate (113 mmoles). The resulting slurry was stirred at ambient temperature overnight, diluted with 125 ml of hexane and filtered. The combined filtrate was concentrated to a yellow syrup. Flash chromatography of the yellow syrup over 250 g silica gel with 1.5 L of 7% ETOAC/Hexane, 2 L of 15% ETOAC/Hexane and 2 L of 25% ETOAC/Hexane, 1.5 L of 10% MeOH/CH₂Cl₂ gave 11.88 g of the 2-monobenzyl ether of the starting material (74.5% yield) and 2.03 g of unreacted starting material MS: [M+H]⁺: 181.

b. Mitsunobu Reaction

The 2-monobenzyl ether of Example 15(a), 5.4 g, was converted into 6.6 g of the 3-benzoate ester (yield 66.9%) by Mitsunobu reaction in accordance with the procedure of Example 19(a); MS: [M+H]⁺=330.

c. Alkaline Hydrolysis

The 5.3 g of the product of Example 15(b) was subjected to alkaline hydrolysis according to the procedure of Example 19(b) to give 2.33 g of the 2-monobenzyl ether of (2R,3S)-2,3-butanediol (yield 80.3%) (M+H)⁺=181; [α]$_D^{23}$=−23.750° (CHCl₃; c=1)

d. Formation of the SEM Ether

To a stirred solution of 3.14 g of the product of Example 15(c) (17.44 mmoles) and 3.8 ml of di-isopropylethylamine (2.82 g, 21.8 mmoles) in 30 ml of anhydrous CH₂Cl₂ at ambient temperature were added 3.8 ml of SEM-Cl (3.64 g, 21.8 mmoles) in one portion. Fuming formed and the resulting yellow solution was stirred for 20 hours. The orange-colored reaction mixture was evaporated under

EXAMPLE 14

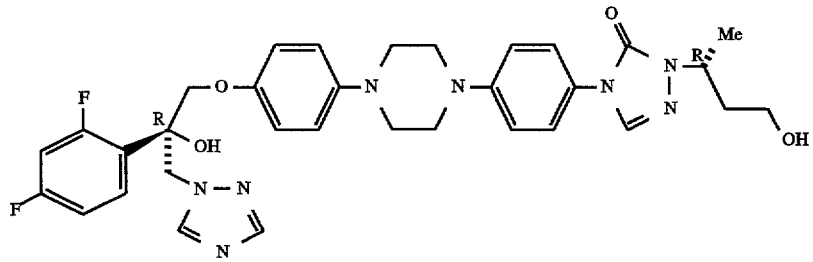

Follow the procedures of Example 14 except substitute an equivalent amount of S-(+)-1,3-butanediol for the corresponding R enantiomer to obtain the title compound in four steps.

EXAMPLE 15 reduced pressure and the solid residues were partitioned between ether and water. The ethereal solution was washed once with distilled water, saturated brine, dried over mg 504 and concentrated to give the crude product. Flash chromatography of the crude product over 200 g silica gel with 2 L of 3% ETOAC/Hexane gave 5.3 g of the 3-O-SEM ether of

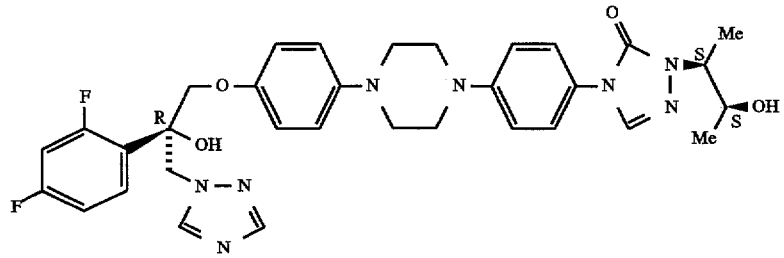

a. Benzylation

To a solution of 10 g of (2R, 3R)-(−)-2,3-butanediol (111 mmoles) in 40 ml of anhydrous CH₂Cl₂ and 80 ml of cyclohexane at 0° C. were added 1 ml of trifluoromethanesulfonic acid (TfOH), followed by dropwise addition of 21 the product of Example 22(c) (98% yield) as a colorless liquid; MS: [M+H]⁺=311.

e. Hydrogenolsis

A mixture of 5.25 g of the product of Example 15(d) (16.94 mmoles) and 0.5 g of 10% Pd/C in 150 ml of methanol was hydrogenated under atmospheric pressure for 6 hours. Catalysts were filtered and washed with additional methanol. The combined filtrate was concentrated to give a-colorless liquid. Flash chromatography of the liquid over 100 g silica gel with 2 L of 10% ETOAC/hexane 3.53 g of the free alcohol (yield 95%) as a colorless liquid; MS: 174, 103.

f. Brosylation

The product of Example 15(e) 1 g was converted into 1.52 g of the corresponding brosylate in 76.2% yield in accordance with the procedure of 11(b); $[\alpha]_D^{23}=-53°$ (CHCl$_3$; c=1)

g. Alkylation Reaction

React the brosylate of Example 15(f), 1.48 g with the product of Example 9 to give of the 2-alkylated triazol-3-one.

h. Acidic Hrydrolysis

Hydrolyze the product of Example 15(g) in accordance with the procedure of Example 11(d) to give the title compound.

EXAMPLE 16

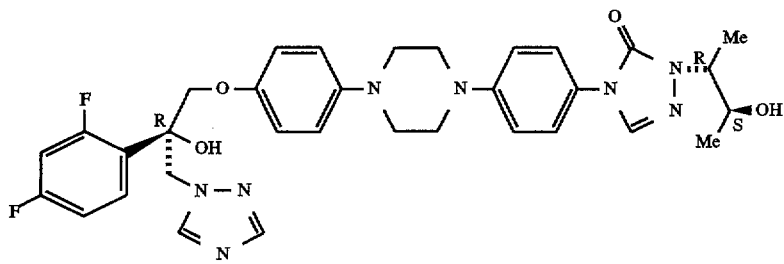

a. Mitsunobu Reaction

The product of step e of Example 15(1.99 g, 9.05 mmoles) was reacted with p-nitrobenzoic acid in accordance with the procedure Example 19(a) to give 3.3 g of product (yield 98.8%); MS=[M+H]$^+$=221.

b. Alkaline Hydrolysis

The product of step (a) of this Example (2.36 g, 6.4 mmoles) was hydrolyzed by 7 ml of 1N NaOAc to give 1.18 g of the 3-O-SEM ether of (2S,3S)-2,3-butanediol (yield 83.7%). MS: [M+H]$^+$=221 $[\alpha]_D^{23}$=+55.15° (CHCl$_3$; C=1)

c. Brosylate Formation

The product of step (b) of this Example (1.15 g were converted into the brosylate in accordance with the procedure of Example 11(b) to give 3.47 g of the brosylate (yield 97.7%).

d. Alkylation and Acidic Hydrolysis

Follow the procedures of Example 11(c) and (d) except substitute the product of Example 16(c) for that of 11(b) to give the title compound.

EXAMPLE 17

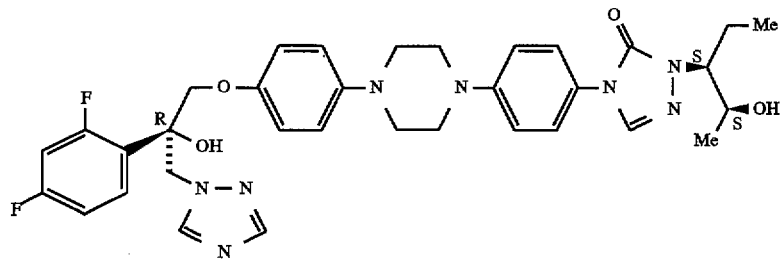

a. The methyl ester of (S)-lactic acid was converted into the corresponding benzyloxymethyl ether in accordance with the procedure of W. C. Still, et al. Tetrahedron Letters, 21, 1035–1038(1980).

b. Reduction to the Aldehyde

DIBAL-H, 37.7 ml of a 1M solution, was added dropwise to a stirred solution of 7.67 g of the ester of step (a) of this Example in toluene at −78° C. (dry ice/acetone bath) under an atmosphere of nitrogen. After 6 min. methanol (10 ml) followed by an aqueous solution of Rochelles salt were added. After warming to room temperature the moisture was partitioned between ETOAc and water. The organic phase was separated, washed with water, dried (MgSO$_4$) and concentrated to produce the crude aldehyde which was used in the next step without purification.

c. Grignard Step

The THF solution of 80 ml of 1 molar solution of the ethyl magnesium bromide Grignard reagent was added dropwise to a stirred THF solution of the crude aldehyde obtained from step (b) of this Example at −78° C. (dry ice/acetone bath) under an atmosphere of nitrogen. After the addition was complete, the resulting mixture was allowed to warm slowly to room temperature overnight and stirred for a further period of 48 h. An aqueous solution of Rochelles salt was added and then the resulting mixture was partitioned between acetone and water. The organic phase was separated, washed with water, dried (MgSO$_4$) and concentrated. The residue was purified by column chromotography on silica gel using ETOAC/Hexane (1:10) as eluant to give (i) non-polar alcohol (2S,3S) 2.31 g; 31%, as a colorless oil.

(ii) a mixture of both alcohols, 1.23 g; 41% and (iii) polar alcohol (2S,3R) 1.23 g; 16%, as a colorless oil.

d. Brosylation of polar alcohol

4-Bromobenzenesulphonyl chloride (1.035 g, 4.1 mmoles) was added to a stirred solution of (0.605 g, 2.7 mmoles) the polar (2S, 3R) alcohol of step (b) of this Example and 2.20 g (5.9 mmoles) of DMAP in CH$_2$Cl$_2$ at room temperature under an atmosphere of nitrogen. The resulting mixture was stirred for 12 h. and then partitioned between ETOAC and water. The organic phase was separated, washed with water, dried and concentrated. The residue was purified by column chromatography on silica gel using ETOAC/Hexane (1:10) as eluant to give the desired brosylate (85%) as a colorless oil.

e. Alkylation and acidic hydrolysis

Follow the procedures of Example 11(c) and (d) except substitute the (2S, 3R) bosylate of step (c) of this Example for that used in Example 11(c). The Acidic hydrolysis produces the title compound.

EXAMPLE 18

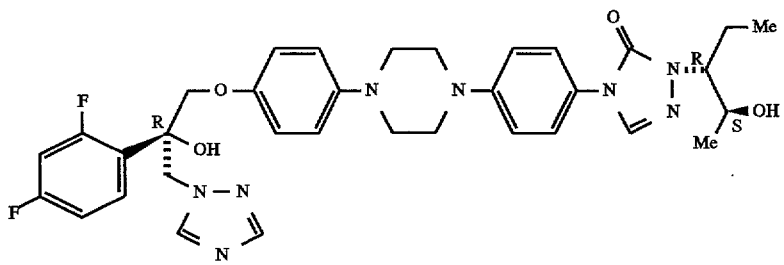

The procedures of Example 17 were followed except the non-polar (2S,3S) alcohol from step (b) of Example 17 was converted into the (2S,3S)-3-brosylate. Alkylation of the brosylate followed by acidic hydrolysis of the SEM protecting group in accordance with the procedures of Example 17(d) provides the title compound.

EXAMPLE 19

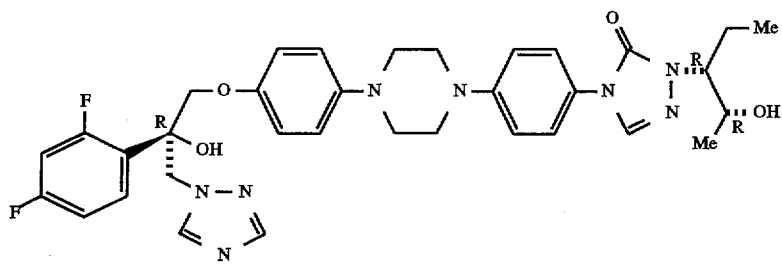

The procedures of Example 17 were followed except the methyl ester of (R) lactic ester was substituted for the methyl ester of (S)-lactic acid in step (a) of Example 17. Use the (2R, 3S) alcohol in steps (c) and (d) to provide the title compound.

EXAMPLE 20

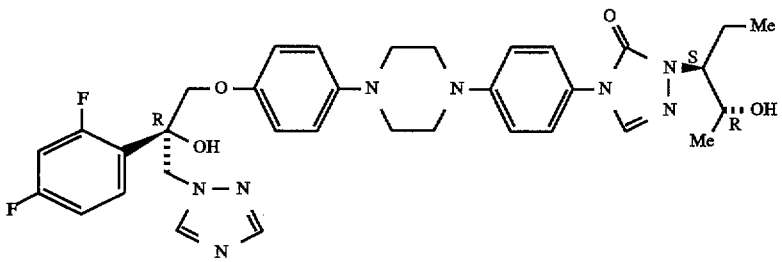

Follow the procedures of Example 19 except use the (2R, 3R) alcohol in steps (c) and (d) to provide the title compound.

EXAMPLE 21

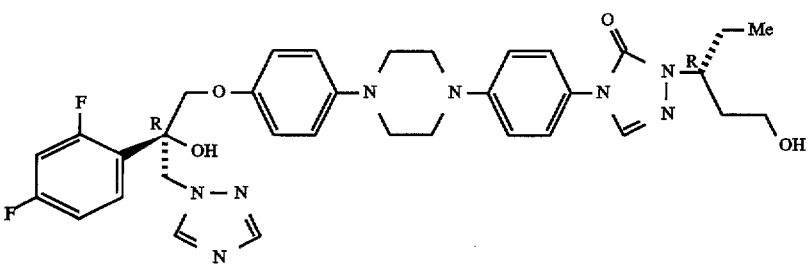

a. Reduction

To methyl (3R)-hydroxyvalerate (5.289, 40.0 mmoles) dissolved in 100 ml of anhydrous THF at 0°–5° C. was added dropwise 60 ml of a 1M THF solution of LiAlH$_4$(60 mmoles). The solution was allowed to warm to ambient temperature and to the so-formed mixture was added sequentially, 2.5 mL of water, dropwise, 2.5 mL of 15% NaOH and 7.5 mL of water. The so-formed reaction mixture was stirred at ambient temperature for 4 h. The inorganic solids were removed by filtration and the filtrate was evaporated to give of (3R)-1,3-pentanediol.

b. 1-O-SEM ether formation

The procedure of Example 11(a) was followed except an equivalent quantity of the product of step (a) of this Example was substituted for the (2R, 3R)-2,3-butanediol to provide the title compound.

c. Mitsunobu Reaction

The procedure of Example 12(a) was followed except that an equivalent quantity of the product of step (b) of this Example was substituted for the 2-SEM ether of (2R,3R)-2,3-butanediol to give 3.34 g of the corresponding p-nitrobenzoate.

d. Basic Hydrolysis

The procedure of Example 12(b) was followed except that an equivalent quantity of the p-nitrobenzoate ester of step (c)

of this Example was used to provide 1.88 g of the 1-O-SEM ether of (3S)-1,3-pentanediol.

e. Brosylation, Alkylation and Acid Hydrolysis

Follow the procedures of Example 11 (b), (c), and (d) except substitute an equivalent quantity of the product of step (d) of this Example for the corresponding 1-O-SEM ether of (2R, 3R) 2,3-butanediol used in Example 12(b) to produce the title compound of this Example

EXAMPLE 22

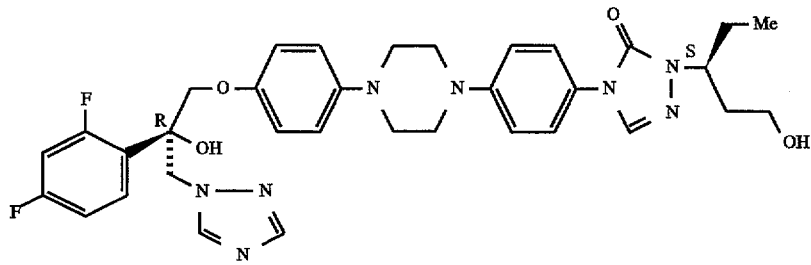

The procedures (a) and (b) of Example 21 were followed to produce the 1-O-SEM-(3R)-1,3-pentanediol which was converted directly into the 3R brosylate by following the procedures of Example 11(b). Use the 3R brosylate to alkylate the product of Example 9 in accordance with the procedures of Example 11(c). Subject the so-formed product to acidic hydrolysis in accordance with the procedures of Example 11(d) to provide the title compound.

EXAMPLE 23

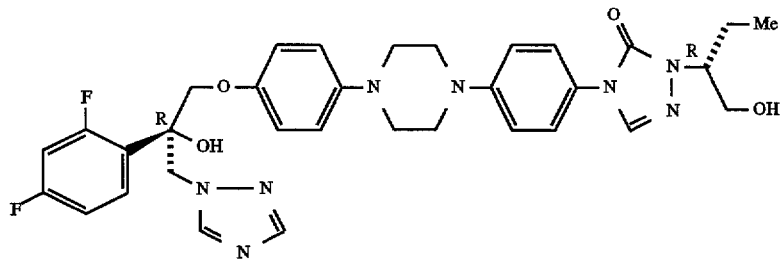

a. Preparation of (2S)-1,2-butanediol

A solution of (2S)-3-butene-1,2-diol which was purchased from Eastman Kodak, (3 g, 0.034mmoles) in 40 mL of ethanol was hydrogenated in the presence of 300 mg of 10% Pd/C overnight. The so-formed reaction mixture was filtered through celite. The so-formed filter cake was washed with ethanol and the combined filtrates were evaporated to provide 2.08 g (68% yield) of the title compound.

b. 1O-SEM ether formation, brosylation, alkylation and acidic hydrolysis

Follow the procedures of Example 11(a)–(d) except substitute an equivalent amount of the product of step (a) of this Example for the (2R, 3R)-2,3-butanediol of Example 11 to provide the compound of this example.

EXAMPLE 24

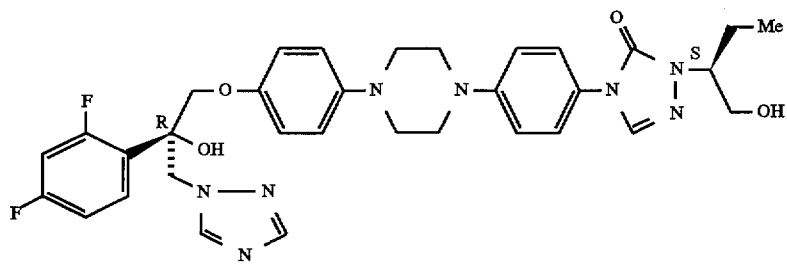

Follow the procedures of Example 24 except substitute an equivalent quantity of (2R)-3-butene-1,2-diol (available from Eastmand Kodak) for (2S)-3-butene-1,2-diol in step (a) of Example 23. Then follow the procedures of Example 23(b) to produce the compound of this example.

EXAMPLE 25

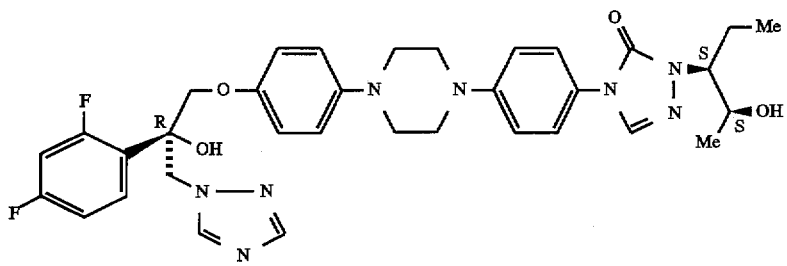

a. (S)-2-(benzyloxy) propionaldehyde by selective reduction of (S)-(O-benzyl) lactic acid pyrrolidine amide To a solution of the S-(O-benzyl)lactic acid pyrrolidene amide prepared in accordance with the procedure of Tetrahedron, 1989, vol. 45, pages 57–67(5 g, 0.0214 mol.) dissolved in 20 ml of toluene cooled to in a ice methanol bath was added slowly with stirring 4.25 ml or RED-AL (3.4 M solution of sodium bis(2-methoxyethoxy) aluminum hydride) in toluene available from Aldrich Chemical Catalogue #19, 619–3). The solution was stirred for 5 hrs., quenched with 2.5 ml of acetone and thereafter with 35 ml of 2NHCl. The so-formed mixture was extracted with EtoAc. The organic extracts were washed with water, NaHCO$_3$ and brine, dried over Na$_2$SO$_4$ and evaporated to give the titled product.

b. (S)-2(Benzyloxy)-N-(Formylamino) propanimine

The propionaldehyde of step (a) (1 g, 16.09 mml) was added dropwise to a solution of formyl hydrazine (0.73 g, 12.18 mmol) dissolved in 5 ml of methanol. The so-formed reaction mixture was stirred overnight. The solvent was removed by evaporation and the so-formed residue was stirred with ethyl ether. The undissolved excess formyl hydrazine was removed by filtration and the ether was removed to provide a residue which was chromatographed on silica gel(/) using 20% (v:v) to give 805 mg of the title product as a light yellow waxy solid having strong UV activity; ms [M +H]$^+$=207.

c. 2-[3-(2S, 3S)-2-(Benzyloxy)pentyl]formic acid hydrazide

Ethylmagnesium bromide (1.3 ml, 3.9 mmol, 3.0 molar in ethyl ether) was added to a stirred solution of 200 mg, 0.97 mmol of the propanimine of step (b) in 10 ml of ethyl ether at 0° C. The so-formed reaction mixture was stirred overnight at room temperature and quenched with water. The organic layer was separated and the solvent removed to provide a residue which was chromatographed on silica gel using 30 to 50% of EtoAc:hexane (v:v) to provide 113 mg; (50 % yield) of the title compound as an oil. The ratio of S,S isomer: S,R isomer in the product was 94:6. When the reaction was repeated in the presence of 1.2 equivalent of bis(trimethylsilyl) acetamide the S,S:S,R ratio improved to 99:1 MS: [M +H]$^+$=237 d. Cyclization Reaction

Stir a solution of 156.3 mg, 0.66 mmol of the product of step (c) and 400 mg 0.60 mmol of 13F of Scheme IIB and I mole of DBU (1,8-diaza bicyclo [5.4.0]undec-7-ene) in toluene at 80° C. for six hours; raise the temperature to 100° to 110° C. and stir continuously at this temperature overnight. Allow the reaction mixture to cool to room temperature and continue the stirring over the weekend. Remove the solvent by evaporation and purify the crude product on preparative TLC (80% EtoAc) hexane, v:v) to provide the benzyl ether of the title product of this example.

e. Hydrogenolysis

Add to the solution of the benzyl ether (190 mgs, 0.24 mmol) of step d dissolved in 10 ml of methanol 40 mg of Pd black on carbon and 4 ml of formic acid. Seal the reaction flask with a ballon and heat it at 60° C. for four hours. Remove the catalyst by filtration through a celite cake and pour the filtrate into cold water. Adjust the pH of the so-formed solution to a value of 4 to 5 with ammonia. Extract the so-formed mixture with EtOAc. Separate the organic layer and dry it over Na$_2$SO$_4$. Remove the solvent to provide a crude product which may be purified on preparative TLC (5% methanol: CH$_2$CL$_2$, v:v) to give the title compound of this example.

EXAMPLE 26

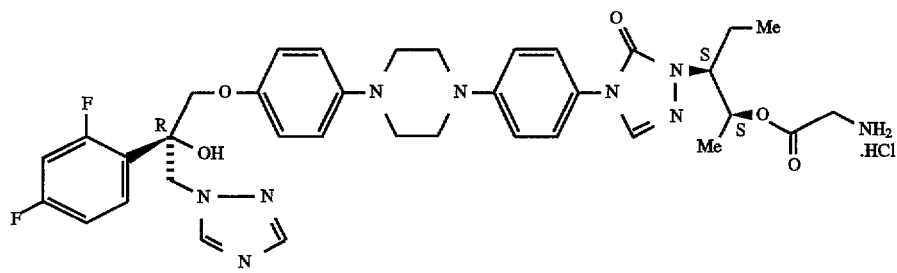

A. To a solution of N-Cbz-glycine (315 mg), N,N-dimethylaminopyridine (DMAP, 200 mg), and compound of Example 17 (900 mg) in $CH_2Cl_2$ (50 mL) at 0° C., add dicyclohexylcarbodiimide (DCCD, 290 mg). Stir the solution at 0° C. for 30 min., then at room temperature for 1 hr. Add additional N-Cbz-glycine (700 mg) and then increments of DCCD at 20 min. intervals until the reaction is complete by TLC. Pour the reaction mixture into 5% aqueous $KH_2PO_4$ and extract with EtOAc. Wash the EtOAc extracts three times with 5% aqueous $KH_2PO_4$, then with brine, and dry the extracts over anhydrous $MgSO_4$. Filter, evaporate the filtrate, and chromatograph the residue to obtain the N-Cbz-glycinyl ester.

B. Stir a solution of the N-Cbz-glycinyl ester of step A above in 100 mL MeOH-96% HCOOH (10:1) in sealed flask with a safety valve. Add 30 mg increments of palladium b lack at 30 min intervals until the reaction is complete by TLC (6–14 hr.). Suction-filter the mixture, add 12N HCl (0.5 mL) to the filtrate and evaporate the so-formed mixture to dryness. Add water (100 mL) and activated carbon (0.8 g) to the residue, suction-filter on a 0.451 μ nylon membrane. Lyophilize the filtrate to provide the title compound.

EXAMPLE 27

Follow the procedure of Example 33 except substitute an equivalent amount of any other N-carbonbenzoxy or N-tert-butoxycarbonyl protected natural amino acid to obtain the corresponding natural α-amino acid ester hydrochloride of the compound of Example 32.

EXAMPLE 28

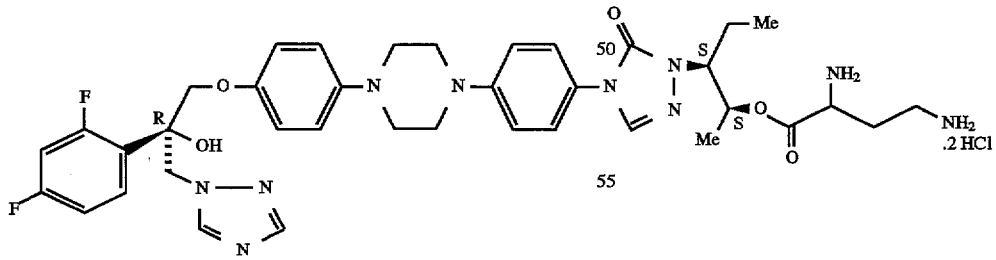

Follow the procedure of Example 26 except substitute an equivalent quantity of N,N'-dicarbobenzoxy 2,4-diaminobutanoic acid for N-Cbz-glycine to obtain the title compound.

EXAMPLE 29

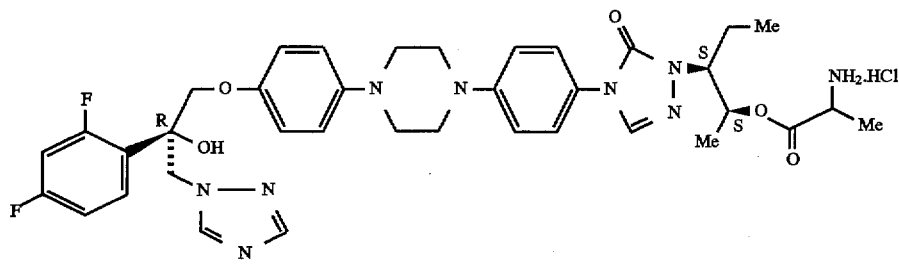

Follow the procedure of Example 26 except substitute an equivalent quantity of N-carbobenzoxy-L-alanine for N-Cbz-glycine to obtain the title compound.

EXAMPLE 30

The preferred compounds of formula 20F may be prepared in accordance with the procedures of Examples 1–25 and Schemes I–II, IIA and IIB are listed hereinbelow:

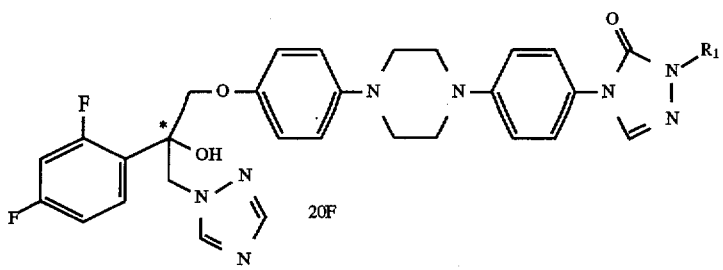

wherein $R_1$ is:

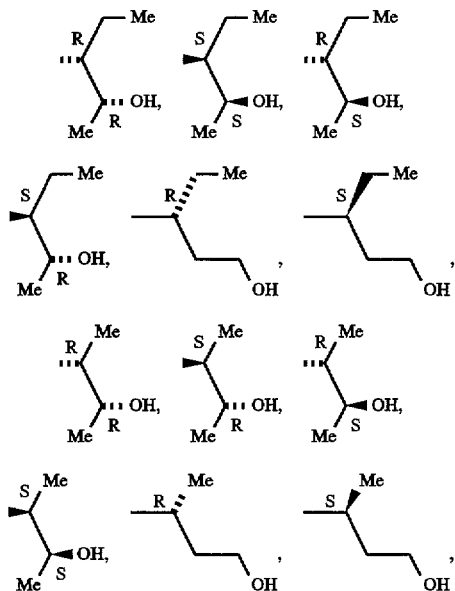

-continued

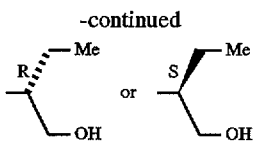

the above-listed compound 20F wherein $R_1=$

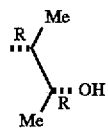

may be prepared by substitution of an equivalent amount of (2R,3R)-2,3-butanediol for the 2-monobenzyl ether of (2R, 3S) butanediol used in step a of Example 15. Treat the product so formed in accordance with the procedures of steps f, g, and h of Example 15. The above-listed compound 20F wherein

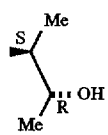

may be prepared by substitution of an equivalent amount of the 2-O-SEM ether of 2R,3R butanediol for the starting material used in step d of Example 15. The product so formed was thereafter treated in accordance with the procedures of steps c, f, g, and h of Example 15.

The compounds of formula 20F wherein the asterisk carbon has the S absolute configuration may be prepared by substituting the compound of Example 10 for the compound of Example 9 and following the above procedures.

What is claimed is:

1. A compound represented by the formula I

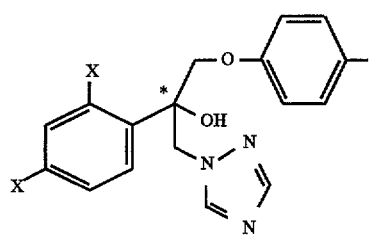

[I]

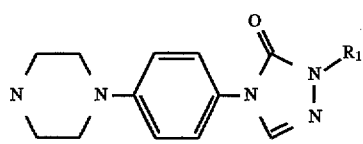

wherein

X is independently both F or both Cl or one X is independently F and the other is independently Cl;

$R_1$ is a straight or branched chain ($C_3$ to $C_8$) alkyl group substituted by one or two hydroxy moieties; and esters and ethers thereof wherein the carbon with the asterisk (*) may have the R or S absolute configuration; or a pharmaceutically acceptable salt thereof.

2. A compound of claim 1 wherein $R_1$ is a straight or branched chain ($C_4$-$C_5$) alkyl group substituted by at least one hydroxy moiety.

3. A compound of claim 1 wherein $R_1$ is $CHR_2R_3$ and which is represented by the formula II

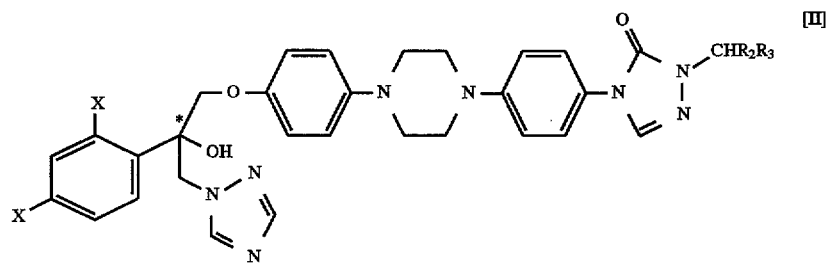

[II]

wherein $R_2$ is H or ($C_1$-$C_3$) alkyl and $R_3$ is ($C_1$-$C_3$) alkyl substituted by one hydroxy moiety and the carbons with the asterisks (*) have the R or S absolute configuration;

an ester or ether thereof or a pharmaceutically acceptable salt thereof.

4. A compound of claim 1 wherein $R_1$ is $CHR_2R_3$ and which is represented by the formula IIa

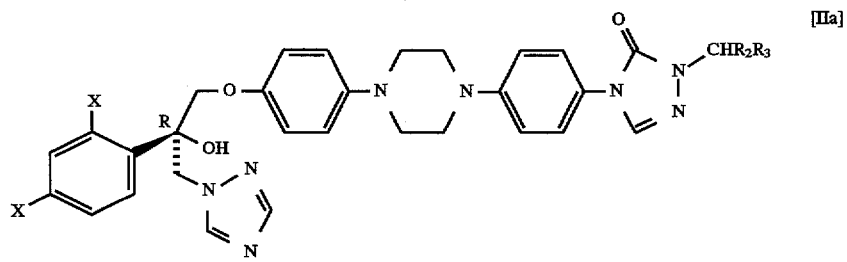

[IIa]

wherein

X is independently both F or both Cl or one X is independently F and the other is independently Cl;

wherein

X is independently both F or both Cl or one X is independently F and the other is independently Cl; wherein $R_2$ is H or $(C_1-C_3)$ alkyl and $R_3$ is $(C_1-C_3)$ alkyl substituted by one hydroxy moiety and the carbon with the asterisk (*) has the R or S absolute configuration;

an ester or ether thereof or a pharmaceutically acceptable salt thereof.

5. A compound of claim 3 wherein $R_2$ or $R_3$ is $(C_1-C_2)$ alkyl and each X is F.

6. A compound of claim 1 wherein $R_1$ is a hydroxy-substituted $C_4$- or $C_5$-alkyl group selected from:

—$\underline{C}$H($C_2H_5$)$\underline{C}$H($R_4$)$CH_3$, —$\underline{C}$H($C_2H_5$)$CH_2CH_2R_4$, —$(CH_2)_2$—$\underline{C}$H($R_4$)$C_2H_5$, —$\underline{C}$H($CH_3$)$\underline{C}$H($R_4$)$CH_3$, —$\underline{C}$H($C_2H_5$)$CH_2R_4$ and —$\underline{C}$H($CH_3$)$CH_2CH_2R_4$ wherein $R_4$ is OH or an ester thereof and the carbons with the asterisk(*) have the R or S absolute configuration or a pharmaceutically acceptable salt thereof.

7. A compound represented by formula III

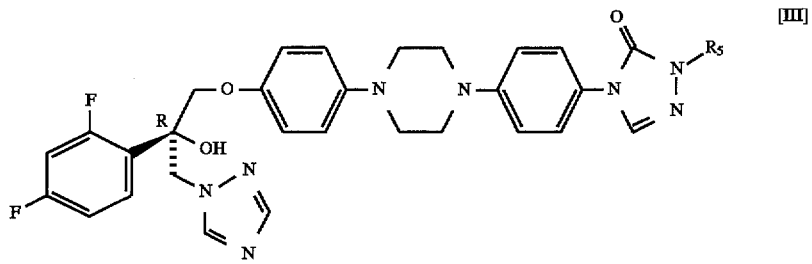

[III]

wherein $R_5$ is

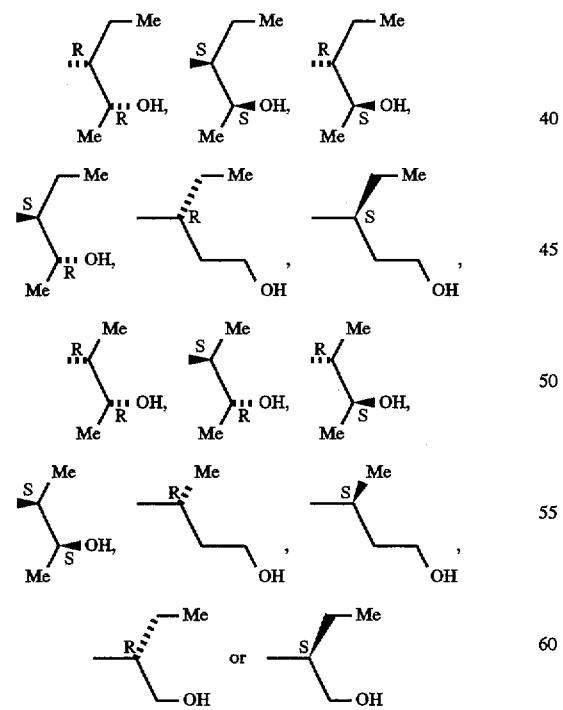

or an ester thereof or a pharmaceutically acceptable salt thereof.

8. A compound represented by the formula IV

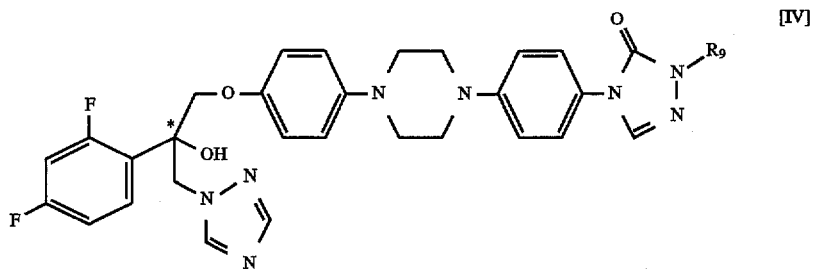

wherein

R₉=—CH(C₂H₅)CH(R₆)CH₃ or —CH(CH₃)CH(R₆)CH₃
wherein

R₆ =is OH, and the carbons with the asterisks (*) have the R or S absolute configuration; or an ester or ether thereof or a pharmaceutically acceptable salt thereof.

9. A compound represented by the formula IVa

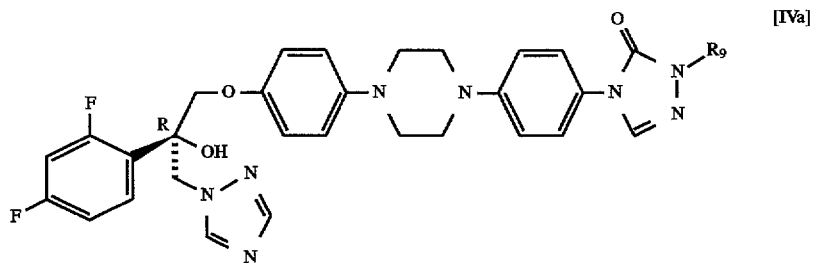

wherein R₉=

—CH(C₂H₅)CH(R₆)CH₃ or —CH(CH₃)CH(R₆)CH₃
wherein

R₆ is OH, and the carbon with the asterisk (*) has the R or S absolute configuration; or an ester thereof or a pharmaceutically acceptable salt thereof.

10. A pharmaceutical composition for treating or preventing fungal infection comprising an antifungally effective amount of a compound of claim 1 together with a pharmaceutically acceptable carrier therefor.

11. A method of treating and/or preventing fungal infections in a mammal afflicted with same which comprises administering an antifungally effective amount of a compound of claim 1 sufficient for such treating or preventing.

12. The pharmaceutical composition of claim 10 wherein the mode of administration is oral or parenteral.

13. The compound of claim 1 wherein the ester is a polyether ester.

14. The compound of claim 7 wherein the ester is a polyether ester.

15. The compound of claim 1 wherein the ester is an amino acid ester.

16. The compound of claim 7 wherein the ester is an amino acid ester.

17. The compound of claim 7 wherein the amino acid ester is derived from reaction of glycine and a compound of formula III.

18. The compound of claim 1 wherein the ester is a phosphate ester.

19. The compound of claim 7 wherein the ester is a phosphate ester.

* * * * *